(12) United States Patent
Parkar et al.

(10) Patent No.: US 11,389,276 B2
(45) Date of Patent: Jul. 19, 2022

(54) PHOTOPOLYMERIZABLE COMPOSITIONS INCLUDING A URETHANE COMPONENT AND A MONOFUNCTIONAL REACTIVE DILUENT, ARTICLES, AND METHODS

(71) Applicant: 3M INNOVATIVE PROPERTIES COMPANY, St. Paul, MN (US)

(72) Inventors: Zeba Parkar, Marietta, GA (US); Jonathan E. Janoski, Woodbury, MN (US); Carla S. Thomas, Woodbury, MN (US); Robert J. DeVoe, Minnetonka, MN (US); Ahmed S. Abuelyaman, Woodbury, MN (US); Eric W. Nelson, Stillwater, MN (US); Richard B. Ross, Cottage Grove, MN (US); John M. Riedesel, San Jose, CA (US)

(73) Assignee: 3M Innovative Properties Comany, St. Paul, MN (US)

( * ) Notice: Subject to any disclaimer, the term of this patent is extended or adjusted under 35 U.S.C. 154(b) by 49 days.

(21) Appl. No.: 16/753,871

(22) PCT Filed: Nov. 9, 2018

(86) PCT No.: PCT/US2018/060014
§ 371 (c)(1),
(2) Date: Apr. 6, 2020

(87) PCT Pub. No.: WO2019/103855
PCT Pub. Date: May 31, 2019

(65) Prior Publication Data
US 2020/0362157 A1 Nov. 19, 2020

Related U.S. Application Data

(60) Provisional application No. 62/589,707, filed on Nov. 22, 2017.

(51) Int. Cl.
*C08F 2/46* (2006.01)
*C08F 2/50* (2006.01)
(Continued)

(52) U.S. Cl.
CPC ............ *A61C 13/0013* (2013.01); *A61C 7/08* (2013.01); *A61K 6/79* (2020.01); *A61K 6/893* (2020.01); *B29C 64/135* (2017.08); *B29C 64/393* (2017.08); *B33Y 10/00* (2014.12); *B33Y 50/02* (2014.12); *B33Y 70/00* (2014.12); *B33Y 80/00* (2014.12); *C08F 220/1808* (2020.02); *C08F 290/061* (2013.01); *C08F 290/067* (2013.01);
(Continued)

(58) Field of Classification Search
CPC ......... C08L 75/16; C08L 33/10; C08L 33/08; C08G 18/8175; C08G 18/2825; C08G 18/8116; A61K 6/79; A61K 6/887; A61K 6/893; B29C 64/393; B29C 64/135; B29K 2105/0002; B29K 2075/00; C08F 220/18; C08F 220/301; C08F 220/1811; C08F 220/1804; C08F 220/1808; C08F 220/365; C08F 290/061; C08F 290/067; C08F 290/147; B33Y 70/00; B33Y 50/02; B33Y 10/00; B33Y 80/00; A61C 13/0013; A61C 13/087; A61C 13/082; A61C 7/08
USPC ................ 522/64, 6, 71, 189, 184, 1; 520/1
See application file for complete search history.

(56) References Cited

U.S. PATENT DOCUMENTS

| | | |
|---|---|---|
| 3,429,722 A | 2/1969 | Economy |
| 3,795,524 A | 3/1974 | Sowman |

(Continued)

FOREIGN PATENT DOCUMENTS

| | | |
|---|---|---|
| CN | 101142252 | 3/2008 |
| CN | 104765251 | 7/2015 |

(Continued)

OTHER PUBLICATIONS

Rolland et al, WO2015200201 Machine Translation, Dec. 30, 2015 (Year: 2015).*

(Continued)

*Primary Examiner* — Jessica Whiteley
(74) *Attorney, Agent, or Firm* — Adrian L. Pishko

(57) ABSTRACT

The present disclosure provides a photopolymerizable composition. The photopolymerizable composition includes at least one urethane component, at least one monofunctional reactive diluent, an initiator, and optionally an inhibitor. The present disclosure also provides an article including the reaction product of the photopolymerizable composition. Further, the present disclosure provides a method of making an article. The method includes (i) providing a photopolymerizable composition and (ii) selectively curing the photopolymerizable composition to form an article. The method optionally also includes (iii) curing unpolymerized urethane component and/or reactive diluent remaining after step (ii). Further, methods are provided, including receiving, by a manufacturing device having one or more processors, a digital object comprising data specifying an article; and generating, with the manufacturing device by an additive manufacturing process, the article based on the digital object. A system is also provided, including a display that displays a 3D model of an article; and one or more processors that, in response to the 3D model selected by a user, cause a 3D printer to create a physical object of an article.

17 Claims, 7 Drawing Sheets

(51) Int. Cl.
| | |
|---|---|
| *C08G 61/04* | (2006.01) |
| *A61C 13/00* | (2006.01) |
| *B33Y 10/00* | (2015.01) |
| *B33Y 50/02* | (2015.01) |
| *B33Y 70/00* | (2020.01) |
| *B33Y 80/00* | (2015.01) |
| *B29C 64/393* | (2017.01) |
| *B29C 64/135* | (2017.01) |
| *A61K 6/893* | (2020.01) |
| *A61K 6/79* | (2020.01) |
| *A61C 7/08* | (2006.01) |
| *C08F 290/06* | (2006.01) |
| *C08F 290/14* | (2006.01) |
| *C08G 18/28* | (2006.01) |
| *C08G 18/81* | (2006.01) |
| *C08L 33/08* | (2006.01) |
| *C08L 33/10* | (2006.01) |
| *C08L 75/16* | (2006.01) |
| *C08F 220/18* | (2006.01) |
| *B29K 75/00* | (2006.01) |
| *B29K 105/00* | (2006.01) |

(52) U.S. Cl.
CPC ...... *C08F 290/147* (2013.01); *C08G 18/2825* (2013.01); *C08G 18/8116* (2013.01); *C08G 18/8175* (2013.01); *C08L 33/08* (2013.01); *C08L 33/10* (2013.01); *C08L 75/16* (2013.01); *B29K 2075/00* (2013.01); *B29K 2105/0002* (2013.01)

(56) References Cited

U.S. PATENT DOCUMENTS

| | | | |
|---|---|---|---|
| 4,047,965 | A | 9/1977 | Karst |
| 4,642,126 | A | 2/1987 | Zador |
| 4,652,274 | A | 3/1987 | Boettcher |
| 4,954,462 | A | 9/1990 | Wood |
| 5,185,299 | A | 2/1993 | Wood |
| 5,462,797 | A | 10/1995 | Williams |
| 5,476,749 | A | 12/1995 | Steinmann |
| 5,780,154 | A | 7/1998 | Okano |
| 5,981,621 | A | 11/1999 | Clark |
| 6,017,973 | A | 1/2000 | Tamura |
| 6,025,114 | A | 2/2000 | Popat |
| 6,057,034 | A | 5/2000 | Yamazaki |
| 6,183,593 | B1 | 2/2001 | Narang |
| 6,200,732 | B1 | 3/2001 | Tamura |
| 6,664,306 | B2 | 12/2003 | Gaddam |
| 7,015,286 | B2 | 3/2006 | Heilmann |
| 8,044,235 | B2 | 10/2011 | Nozawa |
| 8,329,776 | B2 | 12/2012 | Hecht |
| 9,205,601 | B2 | 12/2015 | DeSimone |
| 9,295,617 | B2 | 3/2016 | Eckert |
| 9,315,695 | B2 | 4/2016 | Rahim |
| 9,360,757 | B2 | 6/2016 | DeSimone |
| 9,387,056 | B2 | 7/2016 | Wachter |
| 10,492,888 | B2 | 12/2019 | Chen |
| 2007/0031791 | A1 | 2/2007 | Cinader, Jr. |
| 2008/0248442 | A1 | 10/2008 | Raby |
| 2011/0091832 | A1 | 4/2011 | Kim |
| 2012/0046376 | A1 | 2/2012 | Loccufier |
| 2012/0270038 | A1* | 10/2012 | Kim ..................... C08F 222/10 428/336 |
| 2013/0078594 | A1 | 3/2013 | Leslie-Martin |
| 2013/0095446 | A1 | 4/2013 | Andreiko |
| 2014/0131908 | A1 | 5/2014 | Sun |
| 2014/0167300 | A1 | 6/2014 | Lee |
| 2014/0239527 | A1 | 8/2014 | Lee |
| 2014/0356799 | A1 | 12/2014 | Cinader, Jr. |
| 2016/0184189 | A1 | 6/2016 | Hagiwara |
| 2016/0332367 | A1 | 11/2016 | Sun |
| 2017/0007362 | A1 | 1/2017 | Chen |
| 2020/0140614 | A1 | 5/2020 | Parkar |

FOREIGN PATENT DOCUMENTS

| | | | |
|---|---|---|---|
| CN | 105315901 | 2/2016 | |
| EP | 0142172 A2 | 5/1985 | |
| EP | 0 476 789 | 3/1992 | |
| EP | 0562826 | 9/1993 | |
| EP | 2008636 | 12/2008 | |
| EP | 2167013 | 3/2010 | |
| EP | 3040046 A1 | 7/2016 | |
| GB | 2163443 | 2/1986 | |
| GB | 2189793 | 11/1987 | |
| JP | 2001302744 | 10/2001 | |
| JP | 2001-310918 | 11/2011 | |
| WO | WO 1996-15179 | 5/1996 | |
| WO | WO-9615179 A2 * | 5/1996 | ............. A61K 6/893 |
| WO | WO 1998-11142 | 3/1998 | |
| WO | WO 1998-39374 | 9/1998 | |
| WO | WO 2006-044012 | 4/2006 | |
| WO | WO 2009-045752 | 4/2009 | |
| WO | WO 2012-045660 | 4/2012 | |
| WO | WO 2013-052105 | 4/2013 | |
| WO | WO 2014-078537 | 5/2014 | |
| WO | WO 2014-098956 | 6/2014 | |
| WO | WO 2015-094842 | 6/2015 | |
| WO | WO 2015-200201 | 12/2015 | |
| WO | WO-2015200201 A * | 12/2015 | ........... B29C 64/129 |
| WO | WO 2016-071811 | 5/2016 | |
| WO | WO 2016-109660 | 7/2016 | |
| WO | WO 2016-148960 | 9/2016 | |
| WO | WO 2016-149007 | 9/2016 | |
| WO | WO 2016-182444 | 11/2016 | |
| WO | WO 2016-187155 | 11/2016 | |
| WO | WO 2018-005501 | 1/2018 | |
| WO | WO 2019-023009 | 1/2019 | |

OTHER PUBLICATIONS

Ali, "Relationship Between Physical-Mechanical Properties and Glass Transition Temperatures of UV-Cured Polymers", Polymer-Plastics Technology and Engineering, 1998, vol. 37, No. 2, pp. 175-189.
Cavex LC Dental Tray, Apr. 2015, 6 pages.
EBECRYL® 8808 Aliphatic Urethane Diacrylate, Allnex Technical Data Sheet, 2013, 2 pages.
Griffin, "Calculation of HLB Values of Non-Ionic Surfactants", Journal of the Society of Cosmetic Chemists, 1954, vol. 5, pp. 249-259.
Mappes, Types of Orthodontic Appliances, 6 pages.
Matsumoto, "Synthesis and Thermal Properties of Poly (cycloalkyl methacrylate)s Bearing Bridged- and Fused-Ring Structures", Journal of Polymer Science A:, Polymer Chemistry, 1993, vol. 31, pp. 2531-2539.
Tuncay, The Invisalign System, Section III—Performance Characteristics of the Invisalign System, Chapter 20, "Properties of Aligner Materials," pp. 179-185, 2006.
International Search Report for PCT International Application No. PCT/US2018/060014, dated Apr. 8, 2019, 7 pages.

* cited by examiner

PHOTOPOLYMERIZABLE COMPOSITIONS INCLUDING A URETHANE COMPONENT AND A MONOFUNCTIONAL REACTIVE DILUENT, ARTICLES, AND METHODS

CROSS REFERENCE TO RELATED APPLICATIONS

This application is a national stage filing under 35 U.S.C. 371 of PCT/US2018/060014, filed Nov. 9, 2018, which claims the benefit of U.S. Application No. 62/589,707, filed Nov. 22, 2017, the disclosure of which is incorporated by reference in its/their entirety herein.

TECHNICAL FIELD

The present disclosure broadly relates to articles including a urethane component and at least one monofunctional reactive diluent, and methods of making the articles, such as additive manufacturing methods.

BACKGROUND

The use of stereolithography and inkjet printing to produce three-dimensional articles has been known for a relatively long time, and these processes are generally known as methods of so called 3D printing (or additive manufacturing). In vat polymerization techniques (of which stereolithography is one type), the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is often not yet fully cured and must, usually, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

SUMMARY

Existing printable/polymerizable resins tend to be too brittle (e.g., low elongation, short-chain crosslinked bonds, thermoset composition, and/or high glass transition temperature) for a resilient oral appliance such as an aligner. An aligner or other appliance prepared from such resins could easily break in the patient's mouth during treatment, creating material fragments that may abrade or puncture exposed tissue or be swallowed. These fractures at the very least interrupt treatment and could have serious health consequences for the patient. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in both the final cured article. In contrast, compositions for inkjet printing processes need to be much lower viscosity to be able to be jetted through nozzles, which is not the case for most vat polymerization resins.

Urethane (meth)acrylates are a class of raw materials that have interesting properties, for example an elongation of over 100% when cured, and very high toughness. But these resins also have a very high viscosity; at room temperature they are basically solids. Therefore, they only have been used in small amounts in photosensitive resin formulations for vat polymerization or stereolithography, and the properties of these resins are dominated by the other components.

In a first aspect, a photopolymerizable composition is provided. The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a second aspect, an article is provided including a reaction product of a photopolymerizable composition. The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a third aspect, a method of making an article is provided. The method includes (a) providing a photopolymerizable composition and (b) selectively curing the photopolymerizable composition to form an article. Optionally, the method further includes (c) curing unpolymerized urethane component and/or reactive diluent remaining after step (b). The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a fourth aspect, a non-transitory machine readable medium is provided. The non-transitory machine readable medium has data representing a three-dimensional model of an article, when accessed by one or more processors interfacing with a 3D printer, causes the 3D printer to create an article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a fifth aspect, a method is provided. The method includes (a) retrieving, from a non-transitory machine readable medium, data representing a 3D model of an article; (b) executing, by one or more processors, a 3D printing application interfacing with a manufacturing device using the data; and (c) generating, by the manufacturing device, a physical object of the article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a sixth aspect, another method is provided. The method includes (a) receiving, by a manufacturing device having one or more processors, a digital object comprising data specifying a plurality of layers of an article; and (b) generating, with the manufacturing device by an additive manufacturing process, the article based on the digital object. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

In a seventh aspect, a system is provided. The system includes (a) a display that displays a 3D model of an article and (b) one or more processors that, in response to the 3D model selected by a user, cause a 3D printer to create a physical object of an article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Clear tray aligners and tensile bars made according to at least certain embodiments of this disclosure were found to show low brittleness, high elongation, good resistance to water, and good toughness.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
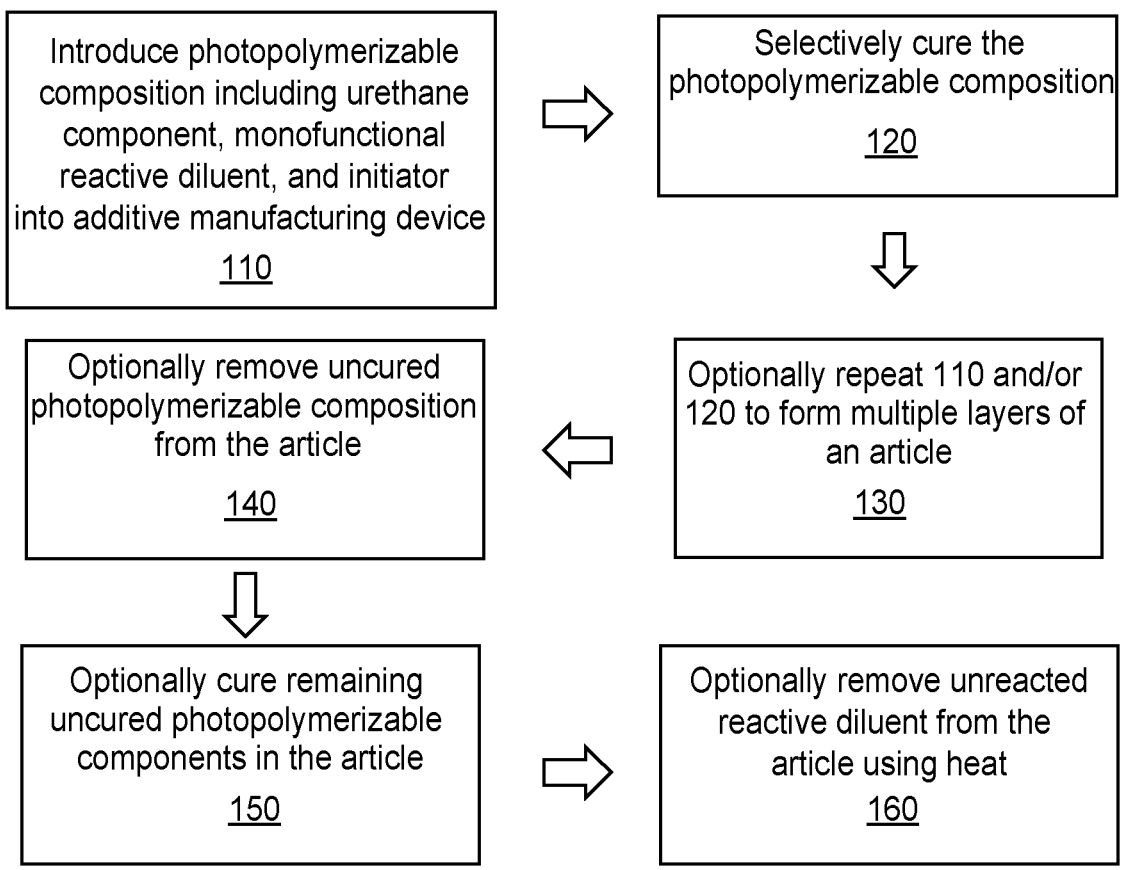
FIG. 1 is a flowchart of a process for building an article using the photopolymerizable compositions disclosed herein.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, the term "hardenable" refers to a material that can be cured or solidified, e.g., by heating to remove solvent, heating to cause polymerization, chemical cross-linking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

As used herein, "oligomer" refers to a molecule that has one or more properties that change upon the addition of a single further repeat unit.

As used herein, "polymer" refers to a molecule having one or more properties that do not change upon the addition of a single further repeat unit.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used. Thermal initiation, using heat and a thermal initiator, can also be employed to initiate polymerization of a polymerizable composition. A combination of actinic radiation and thermal radiation can be used.

As used herein, a "resin" contains all polymerizable components (monomers, oligomers and/or polymers) being present in a hardenable composition. The resin may contain only one polymerizable component compound or a mixture of different polymerizable compounds.

As used herein, a "compatibilizer" refers to a component (e.g., in a polymerizable composition) that improves the interfacial adhesion between two otherwise immiscible material phases. The compatibilizer is present throughout at least one phase, it is preferentially present at an interface between at least two of the phases, and it increases the compatibility of at least two of the phases in the system. If the weight ratio of the compatibilizer in the system is too high relative to the other phases, a portion of it may separately form a distinct phase.

As used herein, "miscible" refers to any (e.g., polymeric) blend having a free energy of mixing less than zero, and "immiscible" refers to any blend having a free energy greater than zero. A miscible polymer is capable of forming a blend with a second material, which blend appears to be a single phase with no apparent phase separation, and such capability may depend on the temperature of the blend.

As used herein, the terms "glass transition temperature" and "$T_g$" are used interchangeably and refer to the glass transition temperature of a material or a mixture. Unless otherwise indicated, glass transition temperature values are determined by Differential Scanning calorimetry (DSC). When the $T_g$ of a monomer or oligomer is mentioned, it is the $T_g$ of a homopolymer of that monomer or oligomer. The homopolymer must be sufficiently high molecular weight such that the $T_g$ reaches a limiting value, as it is generally appreciated that a $T_g$ of a homopolymer will increase with increasing molecular weight to a limiting value. The homopolymer is also understood to be substantially free of moisture, residual monomer, solvents, and other contaminants that may affect the $T_g$. A suitable DSC method and mode of analysis is as described in Matsumoto, A. et. al., J. Polym. Sci. A., Polym. Chem. 1993, 31, 2531-2539.

As used herein the term "hydrophilic-lipophilic balance" and "HLB" are used interchangeably and refer to a characterization of amphiphilic character of a compound.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically cross-linked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least" one of followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, the present disclosure provides a photopolymerizable composition. The photopolymerizable composition comprises a (e.g., miscible) blend of:
a. 30 to 70 wt. %, inclusive, of at least one urethane component;
b. 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius;
c. optionally at least one multifunctional reactive diluent in an amount of 1 to 30 wt. %, inclusive, if present, based on the total weight of the photopolymerizable composition;
d. 0.1 to 5 wt. %, inclusive, of at least one initiator; and
e. an optional inhibitor in an amount of 0.001 to 1 wt. %, inclusive, if present, based on the total weight of the photopolymerizable composition.

The components (a) through (e) are discussed in detail below.

Urethane Component

The photopolymerizable compositions of the present disclosure include at least one urethane component. As used herein, a "urethane component" refers to a compound including one or more carbamate functionalities in the backbone of the compound. In certain embodiments, the carbamate functionality is of Formula I:

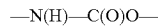

—N(H)—C(O)O—   I.

Urethanes are prepared by the reaction of an isocyanate with an alcohol to form carbamate linkages. Moreover, the term "polyurethane" has been used more generically to refer to the reaction products of polyisocyanates with any polyactive hydrogen compound including polyfunctional alcohols, amines, and mercaptans.

The at least one urethane component provides both toughness (e.g., at least a minimum tensile strength and/or modulus) and flexibility (e.g., at least a minimum elongation at break) to the final article. In some embodiments, in addition to the urethane functionality, the urethane component further comprises one or more functional groups selected from hydroxyl groups, carboxyl groups, amino groups, and siloxane groups. These functional groups can be reactive with other components of the photopolymerizable composition during polymerization. The at least one urethane component often comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof. As used herein, "linking group" refers to a functional group that connects two or more urethane groups. The linking group may be divalent, trivalent, or tetravalent. In select embodiments, the at least one urethane component comprises a urethane (meth)acrylate comprising a polyalkylene oxide linking group, a polyamide linking group, or combinations thereof.

For example, the polymerizable component can include polyfunctional urethane acrylates or urethane methacrylates. These urethane (meth)acrylates are known to the person skilled in the art and can be prepared in a known manner by, for example, reacting a hydroxyl-terminated polyurethane with acrylic acid, methacrylic acid, or isocyanatoethyl methacrylate, or by reacting an isocyanate-terminated prepolymer with hydroxyalkyl (meth)acrylates to give the urethane (meth)acrylate. Suitable processes are disclosed, inter alia, in U.S. Pat. No. 8,329,776 (Hecht et al.) and U.S. Pat. No. 9,295,617 (Cub et al.). Suitable urethane methacrylates can include aliphatic urethane methacrylates, aliphatic polyester urethane methacrylates, and aliphatic polyester triurethane acrylates.

Typically, the urethane component comprises a number average molecular weight (Mn) of 200 grams per mole to 5,000 grams per mole. The number average molecular weight may be measured by matrix assisted laser deposition ionization mass spectrometry (MALDI). The "urethane component" as used herein optionally includes each of a "high Mn urethane component" and a "low Mn urethane component". The high Mn urethane component encompasses compounds including one or more urethane functionalities in the backbone of the compound and that have a number average molecular weight of 1,000 grams per mole (g/mol) or greater, with the proviso that all branches off the backbone of the compound, if present, have a Mn of no more than 200 g/mol. Stated another way, the high Mn urethane component typically has a Mn of 1,000 g/mol or greater, 1,100 g/mol or greater, 1,200 g/mol or greater, 1,300 g/mol or greater, 1,400 g/mol or greater, 1,500 g/mol or greater, 1,600 g/mol or greater, 1,700 g/mol or greater, 1,800 g/mol or greater, 2,000 g/mol or greater, 2,250 g/mol or greater, 2,500 g/mol or greater, 2,750 g/mol or greater, 3,000 g/mol or greater, 3,250 g/mol or greater, 3,500 g/mol or greater, 3,7500 g/mol or greater, or even 4,000 g/mol or greater; and 5,000 g/mol or less, 4,800 g/mol or less, 4,600 g/mol or less, 4,400 g/mol or less, 4,100 g/mol or less, 3,900 g/mol or less, 3,700 g/mol or less, 3,400 g/mol or less, 3,100 g/mol or less, 2,900 g/mol or less, 2,700 g/mol or less, 2,400 g/mol or less, or 2,200 g/mol or less, or even 1,900 g/mol or less.

The low Mn urethane component encompasses compounds including one or more urethane functionalities in the backbone of the compound and that have either 1) a number average molecular weight of 100 g/mol or greater and up to but not including 1,000 g/mol, or 2) a number average molecular weight of 100 g/mol or greater and 2,000 g/mol or less, with the proviso that a number average molecular weight of any one or more linear portions between two reactive groups and/or branches is up to but not including 1,000 g/mol. For instance, a branched urethane component can have a total Mn of greater than 1,000 g/mol but still be a low Mn urethane component due to having a linear segment between two branching points with a Mn of less than 1,000 g/mol. Stated another way, the 1) category of low Mn urethane components typically have a Mn of 100 g/mol or greater, 150 g/mol or greater, 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and up to but not including 1,000 g/mol, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. The 2) category of low Mn urethane components typically have a Mn of 200 g/mol or greater, 250 g/mol or greater, 300 g/mol or greater, 350 g/mol or greater, 400 g/mol or greater, 450 g/mol or greater, 500 g/mol or greater, 550 g/mol or greater, 600 g/mol or greater, 650 g/mol or greater, 700 g/mol or greater, 750 g/mol or greater, or 800 g/mol or greater; and 1,500 g/mol or less, 1,400 g/mol or less, 1,300 g/mol or less, 1,200 g/mol or less, 1,100 g/mol or less, 1,000 g/mol or less, 975 g/mol or less, 925 g/mol or less, 875 g/mol or less, 825 g/mol or less, 775 g/mol or less, 725 g/mol or less, 675 g/mol or less, 625 g/mol or less, 575 g/mol or less, 525 g/mol or less, 475 g/mol or less, or 425 g/mol or less, or even 375 g/mol or less. Each of the foregoing second category of low Mn urethane components includes the proviso that a number average molecular weight of any one or more linear portions between two reactive groups and/or branches is up to but not including 1,000 g/mol, 950 g/mol or less, 900 g/mol or less, 850 g/mol or less, 800 g/mol or less, or 750 g/mol or less; and a number average molecular weight of any one or more linear portions between two reactive groups and/or branches is 100 g/mol or greater, 200 g/mol or greater, 250 g/mol or greater, 300 g/mol or greater, 350 g/mol or greater, 400 g/mol or greater, 450 g/mol or greater, or 500 g/mol or greater.

The use of high Mn urethane components having a number average molecular weight of 1,000 g/mol or greater tend to provide a final article having at least a certain desirable minimum elongation at break (e.g., 25% or greater). Eighty percent by weight or greater of the at least one urethane component is provided by one or more high Mn (e.g., long chain) urethane components. More particularly, in embodiment where a low molecular weight urethane component is present, typical ratios of the high number average molecular weight urethane component to the low number average molecular weight urethane component range from 95:5 high Mn urethane component to low Mn urethane component to 80:20 high Mn urethane component to low Mn urethane component. Stated another way, photopolymerizable compositions according to at least certain aspects of the disclosure include 80 wt. % or more of the total urethane component as a high Mn urethane component, 85 wt. % or more, 87 wt. % or more, 90 wt. % or more, 92 wt. % or more, 95 wt. % or more, or even 97 wt. % or more of the total urethane component as a high Mn urethane component; and 100% or less of the total urethane component as a high Mn urethane component, 98 wt. % or less, 96 wt. % or less, 94 wt. % or less, 91 wt. % or less, 89 wt. % or less, or 86 wt. % or less of the total urethane component as a high Mn urethane component. Similarly, photopolymerizable compositions according to at least certain aspects of the disclosure can include 2 wt. % or more of the total urethane component as a low Mn urethane component, 4 wt. % or more, 5 wt. % or more, 8 wt. % or more, 10 wt. % or more, 12 wt. % or more, 15 wt. % or more, or even 17 wt. % or more of the total urethane component as a low Mn urethane component; and 20 wt. % or less of the total urethane component as a low Mn urethane component, 18 wt. % or less, 16 wt. % or less, 14 wt. % or less, 11 wt. % or less, 9 wt. % or less, 7 wt. % or less, 6 wt. % or less, or 3 wt. % or less of the total urethane component as a low Mn urethane component.

According to certain embodiments, at least one urethane component comprises at least one (meth)acrylate component having a urethane moiety, which may help to improve physical properties of the cured composition like flexural strength and/or elongation at break. Such a urethane component can be characterized by the following features alone or in combination:

a) comprising at least 2 or 3 or 4 (meth)acrylate moieties;
b) number average molecular weight (Mn): from 1,000 to 5,000 g/mol or from 1,000 to 2000 g/mol;
c) comprising a C1 to C20 linear or branched alkyl moiety to which the (meth)acrylate moieties are attached through urethane moieties;
d) viscosity: from 0.1 to 100 Pa·s or 1 to 50 Pa·s at 23° C.

A combination of the features a) and b) or b) and c) or a) and d) can sometimes be preferred.

Urethane (meth)acrylates may be obtained by a number of processes known to the skilled person. The urethane(meth)acrylates are typically obtained by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate. For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and aralipathic isocyanates. Any of the known polyisocyanates such as alkyl and alkylene polyisocyanates, cycloalkyl and cycloalkylene polyisocyanates, and combinations such as alkylene and cycloalkylene polyisocyanates can be employed. Preferably, diisocyanates having the formula $X(NCO)_2$ can be used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an aliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'-methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocyanate, meta- and para-tetra methylxylene diisocycanate, 1,4-phenylene diisocyanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred. Examples of suitable capping agents include 2-hydroxyethyl(meth)acrylate, 2-hydroxypropyl (meth)acrylate, glycerol di(meth)acrylate and/or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

According to select embodiments the urethane dimethacrylate of the following Formulas II and III are preferred:

Examples of commercially available urethane components include those available under the trade designations of EXOTHANE 108 (e.g., including the structure of Formula II), EXOTHANE 8, and EXOTHANE 10 (e.g., including the structure of Formula III) from Esstech Inc, and DESMA from 3M Company. DESMA is described in, e.g., paragraph [0135] and Table 3 of EP2167013B1 (Hecht et al.).

In certain embodiments, a urethane component (e.g., an oligomer or a polymer) may be prepared including one or more pendant groups attached to the urethane backbone. Preferably, at least one pendent group comprises a photoinitiator. For instance, a photoinitiator-containing ethyl acrylate compound (PIEA) has been prepared via the below reaction scheme:

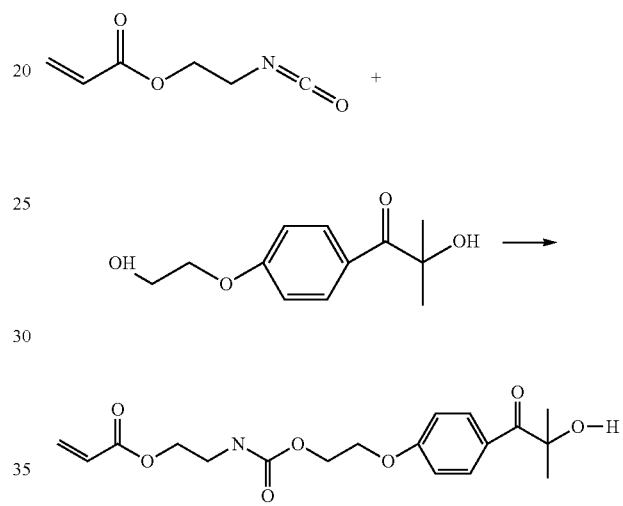

The reaction is described in detail in the Examples below. Next, the PIEA can be reacted with one or more monomers and a thermal initiator in solution, such as per the below reaction scheme:

II

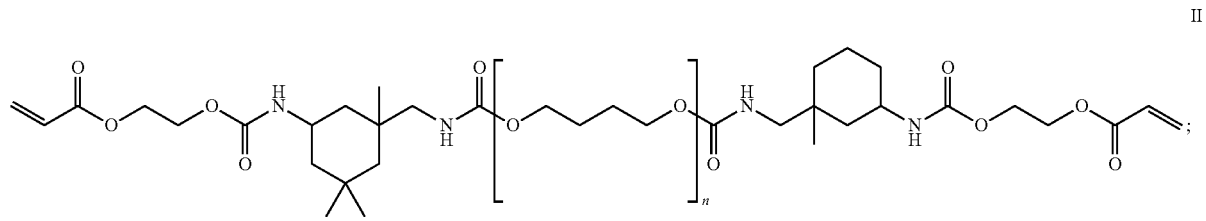

wherein n=9 or 10;

III

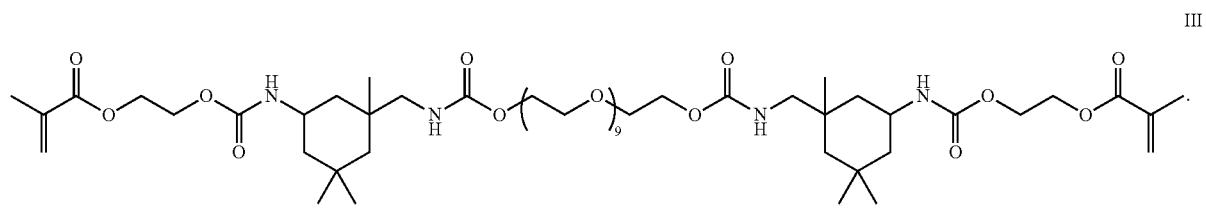

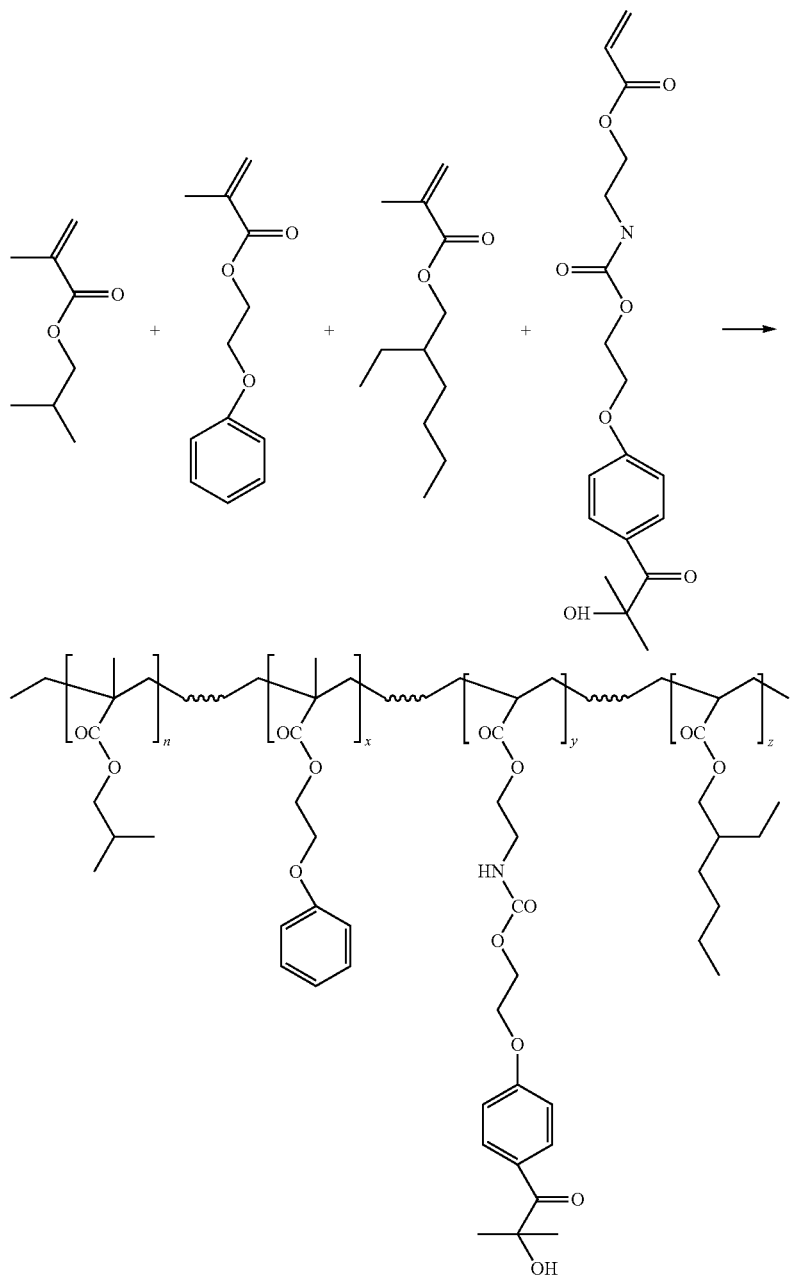

This reaction is also described in detail in the Examples below. Such photoinitiator-carrying urethane components may be included in photopolymerizable compositions of at least certain embodiments of the present disclosure. An advantage to providing the photoinitiator attached to the urethane component is that the location of polymerization at the urethane backbone can be preselected.

The urethane component is included in the photopolymerizable composition in an amount of 50 to 90 wt. %, inclusive, based on the total weight of the photopolymerizable composition, such as 50 to 70 wt. %, inclusive. Typically, the urethane component is included in the photopolymerizable composition in an amount of 50 wt. % or more, 52 wt. % or more, 55 wt. % or more, 57 wt. % or more, 60 wt. % or more, 61 wt. % or more, 62 wt. % or more, 63 wt. % or more, 64 wt. % or more, 65 wt. % or more, 70 wt. % or more, or 72 wt. % or more; and 90 wt. % or less, 87 wt. % or less, 85 wt. % or less, 80 wt. % or less, 77 wt. % or less, or 75 wt. % or less, based on the total weight of the photopolymerizable composition.

Reactive Diluent

The photopolymerizable compositions of the present disclosure include at least one monofunctional reactive diluent. A "reactive diluent," for reference purposes herein, is a component that contains at least one free radically reactive group (e.g., an ethylenically-unsaturated group) that can co-react with the at least one urethane component (e.g., is capable of undergoing addition polymerization). The reactive diluent has a smaller molecular weight than at least one (e.g., high Mn) urethane component, often less than 400 grams per mole, and does not contain any urethane functional groups (e.g., is free of any urethane functional groups).

The reactive diluent comprises at least one monofunctional reactive diluent having a $T_g$ of up to but not including 25° C., 20° C., 15° C., or 10° C. As defined above, it is to be understood that the $T_g$ is of a homopolymer of the monofunctional reactive diluent. Statements throughout this disclosure regarding $T_g$ of a material, for instance, a monomer or oligomer, are to be understood to be shorthand for the $T_g$ of a homopolymer of that material (e.g., that monomer or oligomer). Thus, stated another way, the reactive diluent comprises at least one monofunctional reactive diluent whose homopolymer has a $T_g$ of up to but not including 25° C., 20° C., 15° C., or 10° C. The $T_g$ may be 24° C., 23° C., 22° C., 21° C., 20° C., 18° C., 16° C., 14° C., 12° C., 10° C., or 8° C. The inclusion of a low $T_g$ monofunctional reactive diluent tends to lower the $T_g$ of a reaction product of the photopolymerizable composition.

In some embodiments, the at least one monofunctional reactive diluent further comprises a second monofunctional reactive diluent, wherein (a homopolymer of) the second monofunctional reactive diluent has a $T_g$ of 25° C. or greater, 30° C. or greater, 35° C. or greater, or 40° C. or greater. The $T_g$ may be 80° C. or less, 75° C. or less, 70° C. or less, 65° C. or less, 60° C. or less, 55° C. or less, 50° C. or less, or 45° C. or less. It has been unexpectedly found that a balance of physical properties (e.g., strength and elongation at break) can be obtained in a polymerized article when including both a monofunctional reactive diluent having a $T_g$ of less than 25° C. and a monofunctional reactive diluent having a $T_g$ of 25° C. or greater, in certain photopolymerizable compositions according to the present disclosure.

In some embodiments, the monofunctional reactive diluent further comprises a third monofunctional reactive diluent, plus optionally a fourth monofunctional reactive diluent. In an embodiment, the at least one monofunctional reactive diluent comprises one monofunctional reactive diluent having a $T_g$ of up to but not including 25 degrees Celsius and two monofunctional reactive diluents having a $T_g$ of 25 degrees Celsius or greater. In an alternative embodiment, the at least one monofunctional reactive diluent comprises two monofunctional reactive diluents having a $T_g$ of up to but not including 25 degrees Celsius and one monofunctional reactive diluent having a $T_g$ of 25 degrees Celsius or greater.

In select embodiments, the (at least one) monofunctional reactive diluent comprises a (meth)acrylate, an alkyl (meth)acrylate, a phenoxy (meth)acrylate, a hydroxy alkyl (meth)acrylate, or a combination thereof. In some preferred embodiments, the monofunctional reactive diluent comprises phenoxy ethyl methacrylate, such as in an amount of 20 to 80 wt. % of the total amount of the total monofunctional reactive diluent content.

In certain embodiments, the monofunctional reactive diluent comprises an (e.g., amphiphilic) monofunctional reactive diluent. exhibiting a hydrophilic-lipophilic balance (HLB) value of less than 10. Amphiphilic compounds can be characterized by various methodology. One common characterization method, as known in the art, is the hydrophilic-lipophilic balance ("HLB"). Although various methods have been described for determining the HLB of a compound, as used herein, HLB refers to the value obtained by the Griffin's method (See Griffin W C: "Calculation of HLB Values of Non-Ionic Surfactants," Journal of the Society of Cosmetic Chemists 5 (1954): 259). The computations were conducted utilizing the software program Molecular Modeling Pro Plus from Norgwyn Montgomery Software, Inc. (North Wales, Pa.). According to Griffin's method: HLB=20*Mh/M where Mh is the molecular mass of the hydrophilic portion of the molecule, and M is the molecular mass of the whole molecule. This computation provides a numerical result on a scale of 0 to 20, wherein "0" is highly lipophilic. Preferably, an amphiphilic monofunctional reactive diluent useful for at least certain embodiments of the photopolymerizable compositions described herein exhibits a hydrophilic-lipophilic balance (HLB) value of less than 10, 9 or less, 8 or less, 7 or less, 6 or less, 5 or less, 4 or less, 3 or less, or 2 or less; and 0.1 or more, 0.25 or more, 0.5 or more, 0.75 or more, or 1 or more.

Suitable free-radically polymerizable monofunctional diluents include phenoxy ethyl(meth)acrylate, phenoxy-2-methylethyl(meth)acrylate, phenoxyethoxyethyl(meth)acrylate, 3-hydroxy-2-hydroxypropyl(meth)acrylate, benzyl (meth)acrylate, phenylthio ethyl acrylate, 2-naphthylthio ethyl acrylate, 1-naphthylthio ethyl acrylate, 2,4,6-tribromophenoxy ethyl acrylate, 2,4-dibromophenoxy ethyl acrylate, 2-bromophenoxy ethyl acrylate, 1-naphthyloxy ethyl acrylate, 2-naphthyloxy ethyl acrylate, phenoxy 2-methylethyl acrylate, phenoxyethoxyethyl acrylate, 3-phenoxy-2-hydroxy propyl acrylate, 2,4-dibromo-6-sec-butylphenyl acrylate, 2,4-dibromo-6-isopropylphenyl (meth)acrylate, benzyl (meth)acrylate, phenyl (meth)acrylate, tetrahydrofurfuryl (meth)acrylate, alkoxylated tetrahydrofurfuryl acrylate, ethoxylated nonyl phenol (meth)acrylate, alkoxylated lauryl (meth)acrylate, alkoxylated phenol (meth)acrylate, stearyl (meth)acrylate, tetrahydrofurfuryl (meth)acrylate, lauryl (meth)acrylate, isodecyl (meth)acrylate, isooctyl (meth)acrylate, octadecyl (meth)acrylate, tridecyl (meth)acrylate, ethoxylated (4) nonyl phenol (meth)acrylate, caprolactone (meth)acrylate, cyclic trimethylolpropane formal (meth)acrylate, 3,3,5-trimethylcyclohexyl (meth)acrylate, dicyclopentadienyl (meth)acrylate, isobutyl (meth)acrylate, n-butyl (meth)acrylate, ethyl hexyl (meth)acrylate, isobornyl (meth)acrylate, and 2,4,6-tribromophenyl (meth)acrylate.

In some embodiments, a monofunctional reactive diluent acts as a compatibilizer, which improves the interfacial adhesion between two otherwise immiscible material phases (e.g., the urethane component and one or more other reactive diluent(s)). The amount of compatibilizer used is relative to the amount of the urethane component. Typically, a monofunctional reactive diluent compatibilizer is present in a photopolymerizable composition in an amount of 30 wt. % or greater of the amount of the at least one urethane component, or 35 wt. % or greater, or 40 wt. % or greater, of the amount of the at least one urethane component. In certain embodiments of the photopolymerizable composition, the presence of a compatibilizer enables the composition to be a (miscible) blend instead of more than one substantially separate phase. Some monofunctional reactive diluents that can act as compatibilizers include for instance phenoxy ethyl (meth)acrylate, tetrahydrofurfuryl (meth)acrylate, and n-vinyl pyrrolidone.

Suitable free-radically polymerizable multifunctional reactant diluents include di-, tri-, or other poly-acrylates and methacrylates such as glycerol diacrylate, ethoxylated bisphenol A dimethacrylate (D-zethacrylate), tetraethylene glycol dimethacrylate (TEGDMA), polyethyleneglycol dimethacrylate (PEGDMA), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; bis-acrylates of polyesters (e.g., methacrylate-terminated polyesters); the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); polyfunctional (meth)acrylates comprising urea or amide groups, such as those of EP2008636 (Hecht et al.).

The reactive diluent can comprise one or more poly(meth)acrylates, for example, di-, tri-, tetra- or pentafunctional monomeric or oligomeric aliphatic, cycloaliphatic or aromatic acrylates or methacrylates.

Examples of suitable aliphatic poly(meth)acrylates having more than two (meth)acrylate groups in their molecules are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate.

Another suitable class of free radical polymerizable compounds includes aromatic di(meth)acrylate compounds and trifunctional or higher functionality (meth)acrylate compound. Trifunctional or higher functionality meth(acrylates) can be tri-, tetra- or pentafunctional monomeric or oligomeric aliphatic, cycloaliphatic or aromatic acrylates or methacrylates.

Examples of suitable aliphatic tri-, tetra- and pentafunctional (meth)acrylates are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate. Further examples of suitable aromatic tri(meth)acrylates are the reaction products of triglycidyl ethers of trihydroxy benzene and phenol or cresol novolaks containing three hydroxyl groups, with (meth)acrylic acid.

In some cases, a reactive diluent comprises diacrylate and/or dimethacrylate esters of aliphatic, cycloaliphatic or aromatic diols, including 1,3- or 1,4-butanediol, neopentyl glycol, 1,6-hexanediol, dodecane diol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis(4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. In some cases, a reactive diluent described herein comprises one or more higher functional acrylates or methacrylates such as dipentaerythritol monohydroxy pentaacrylate or bis(trimethylolpropane)tetraacrylate.

In some embodiment comprising a multifunctional reactive diluent, one or more multifunctional reactive diluents are present in an amount of 1 to 30 wt. %, inclusive, such as 5 to 20 wt. %, based on the total weight of the photopolymerizable composition. Stated another way, at least one multifunctional reactive diluent may be present in an amount of 1 wt. % or more, 3 wt. % or more, 5 wt. % or more, 10 wt. % or more, or 15 wt. % or more; and 30 wt. % or less, 25 wt. % or less, 20 wt. % or less, or 17 wt. % or less, based on the total weight of the photopolymerizable composition.

In certain other embodiments, the photopolymerizable composition consists essentially of monofunctional components or is free of multifunctional components. This means that the photopolymerizable composition contains 2 wt. % or less of multifunctional components. It was unexpectedly discovered that a significant amount of the monofunctional reactive diluents are incorporated into the reaction product of the photopolymerizable composition during photopolymerization. This means that a relatively small amount of unreacted monofunctional reactive diluent remains in the reaction product and could be extracted from the cured composition, particularly after subjection of the cured composition to a post-cure step. In certain embodiments, 10% or less of unreacted monofunctional reactive diluent is present in a cured or post-cured article.

In select embodiments, two or more reactive diluents are prepolymerized such that up to 10%, up to 15%, or up to 20% of the functional groups of the reactive diluents are reacted prior to inclusion in the photopolymerizable composition. The prepolymerization is typically performed via initiation with a small amount of photoinitiator added to the reactive diluents. One representative prepolymerization process is described in detail in the Examples below. An advantage of prepolymerizing a portion of the reactive diluent(s) is the formation of a semi-interpenetrative polymer network. Also, the prepolymerization tends to assist in producing higher molecular weight chains in the reaction product of the photopolymerizable composition as compared to the same composition that is not prepolymerized.

In certain embodiments, the at least one reactive diluent has a molecular weight of 400 grams per mole or less, 375 g/mol or less, 350 g/mol or less, 325 g/mol or less, 300 g/mol or less, 275 g/mol or less, 225 g/mol or less, or 200 g/mol or less. Including one or more reactive diluents with such molecular weights can assist in providing a photopolymerizable composition that has a sufficiently low viscosity for use with vat polymerization methods. In certain embodiments, the at least one reactive diluent comprises a molecular weight of 200 g/mol to 400 g/mol, inclusive.

The reactive diluent is included in the photopolymerizable composition in an amount of 25 to 70 wt. %, inclusive, based on the total weight of the photopolymerizable composition, such as 30 to 50 wt. %, inclusive. Typically, the reactive diluent is included in the photopolymerizable composition in an amount of 25 wt. % or more, 30 wt. % or more, or 35 wt. % or more; and 70 wt. % or less, 65 wt. % or less, 60 wt. % or less, 55 wt. % or less, 50 wt. % or less, 45 wt. % or less, or 40 wt. % or less, based on the total weight of the photopolymerizable composition.

Additives

Photopolymerizable compositions described herein, in some instances, further comprise one or more additives, such as one or more additives selected from the group consisting of photoinitiators, thermal initiators, inhibitors, stabilizing agents, sensitizers, absorption modifiers, fillers and combinations thereof. For example, the photopolymerizable composition further comprises one or more photoinitiators, for instance two photoinitiators. Suitable exemplary photoinitiators are those available under the trade designations IRGACURE and DAROCUR from BASF (Ludwigshafen, Germany) and include 1-hydroxycyclohexyl phenyl ketone (IRGACURE 184), 2,2-dimethoxy-1,2-diphenylethan-1-one (IRGACURE 651), bis(2,4,6 trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2- morpholinopropan-1-one (IRGACURE 907), Oligo[2-hydroxy-2-methyl-1-[4-(1-methylvinyl)phenyl]propanone] ESACURE ONE (Lamberti S.p.A., Gallarate, Italy), 2-hydroxy-2-methyl-1-phenyl propan-1-one (DAROCUR 1173), 2,4,6-trimethylbenzoyldiphenylphosphine oxide (IRGACURE TPO), and 2,4,6-trimethylbenzoylphenyl phosphinate (IRGACURE TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

A photoinitiator can be present in a photopolymerizable composition described herein in any amount according to the particular constraints of the additive manufacturing process. In some embodiments, a photoinitiator is present in a photopolymerizable composition in an amount of up to about 5% by weight, based on the total weight of the photopolymerizable composition. In some cases, a photoinitiator is present in an amount of about 0.1-5% by weight, based on the total weight of the photopolymerizable composition.

A thermal initiator can be present in a photopolymerizable composition described herein in any amount according to the particular constraints of the additive manufacturing process. In some embodiments, a thermal initiator is present in a photopolymerizable composition in an amount of up to about 5% by weight, based on the total weight of the photopolymerizable composition. In some cases, a thermal initiator is present in an amount of about 0.1-5% by weight, based on the total weight of the photopolymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO 67 (2,2'-azo-bis(2-methybutyronitrile)) VAZO 64 (2,2'-azo-bis(isobutyronitrile)) and VAZO 52 (2,2'-azo-bis(2,2-dimethyvaleronitrile)), and LUCIDOL 70 from Elf Atochem North America, Philadelphia, Pa.

In certain aspects, the use of more than one initiator assists in increasing the percentage of reactive diluent that gets incorporated into the reaction product and thus decreasing the percentage of the reactive diluent that remains uncured. Reaction of monofunctional reactive diluent(s) in particular is desirable to minimize the presence of unreacted diluent in the product following polymerization.

In addition, a photopolymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the photopolymerizable composition, a sensitizer can be present in an amount ranging of about 0.01% by weight or about 1% by weight, based on the total weight of the photopolymerizable composition.

A photopolymerizable composition described herein optionally also comprises one or more polymerization inhibitors or stabilizing agents. A polymerization inhibitor is often included in a photopolymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the photopolymerizable composition. Further, if used, a stabilizing agent is present in a photopolymerizable composition described herein in an amount of about 0.1-5% by weight, about 0.5-4% by weight, or about 1-3% by weight, based on the total weight of the photopolymerizable composition.

A photopolymerizable composition as described herein can also comprise one or more absorption modifiers (e.g., dyes, optical brighteners, pigments, particulate fillers, etc.) to control the penetration depth of actinic radiation. One particularly suitable absorption modifier is Tinopal OB, a benzoxazole, 2,2'-(2,5-thiophenediyl)bis[5-(1,1-dimethylethyl)], available from BASF Corporation, Florham Park, N.J. The absorption modifier, if used, can be present in an amount of about 0.001-5% by weight, about 0.01-1% by weight, about 0.1-3% by weight, or about 0.1-1% by weight, based on the total weight of the photopolymerizable composition.

Photopolymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, Ohio and CAB-O-SIL M5 and TS-720 silica from Cabot Corp., Tuscola, Ill.). Organic fillers made from polymeric materials are also possible, such as those disclosed in International Publication No. WO09/045752 (Kalgutkar et al.).

In certain embodiments, the filler comprises surface modified nanoparticles. Generally, "surface modified nanoparticles" comprise surface treatment agents attached to the surface of a core. In some embodiments, the core is substantially spherical. In some embodiments, the core is at least partially or substantially crystalline. In some embodiments, the particles are substantially non-agglomerated. In some embodiments, the particles are substantially non-aggregated in contrast to, for example, fumed or pyrogenic silica. Generally, surface treatment agents for silica nanoparticles are organic species having a first functional group capable of covalently chemically attaching to the surface of a nanoparticle, wherein the attached surface treatment agent alters one or more properties of the nanoparticle. In some embodiments, surface treatment agents have no more than three functional groups for attaching to the core. In some embodiments, the surface treatment agents have a low molecular weight, e.g., a weight average molecular weight less than 1000 gm/mole.

In some embodiments, the surface-modified nanoparticles are reactive; that is, at least one of the surface treatment agents used to surface modify the nanoparticles of the present disclosure may include a second functional group capable of reacting with one or more of the urethane component and/or one or more of the reactive diluent(s) of the photopolymerizable composition. For purposes of clarity, even when the nanoparticles are reactive, they are not considered to be constituents of the resin component of the photopolymerizable composition. Surface treatment agents often include more than one first functional group capable of attaching to the surface of a nanoparticle. For example, alkoxy groups are common first functional groups that are capable of reacting with free silanol groups on the surface of a silica nanoparticle forming a covalent bond between the surface treatment agent and the silica surface. Examples of surface treatment agents having multiple alkoxy groups include trialkoxy alkylsilanes (e.g., 3-(trimethoxysilyl)propyl methacrylate) and trialkoxy arylsilanes (e.g., trimethoxy phenyl silane).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, Minn.), such as NEXTEL 312, 440, 610 and 720. One presently preferred ceramic fiber comprises polycrystalline $\alpha$-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, Minn.). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al).

Exemplary aluminosilicate fibers are marketed under the trade designations NEXTEL 440, and NEXTEL 720, by 3M Company (St. Paul, Minn.). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the photopolymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Photopolymerizable compositions herein can also exhibit a variety of desirable properties, non-cured, cured, and as post-cured articles. A photopolymerizable composition, when non-cured, has a viscosity profile consistent with the requirements and parameters of one or more additive manufacturing devices (e.g., 3D printing systems). In some instances, a photopolymerizable composition described herein when non-cured exhibits a dynamic viscosity of about 0.1-1,000 Pa·s, about 0.1-100 Pa·s, or about 1-10 Pa·s, using a TA Instruments AR-G2 magnetic bearing rheometer using a 40 mm cone and plate measuring system at 40 degrees Celsius and at a shear rate of 0.1 l/s, when measured according to ASTM D4287, as set forth in the Example Test Method below. In some cases, a photopolymerizable composition described herein when non-cured exhibits a dynamic viscosity of less than about 10 Pa·s, when measured according to modified ASTM D4287.

Articles and Methods

In a second aspect, the present disclosure provides an article. The article comprises a reaction product of a photopolymerizable composition, the photopolymerizable composition comprising a blend of:

a. 30 to 70 wt. %, inclusive, of at least one urethane component;
b. 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius;
c. optionally at least one difunctional reactive diluent in an amount of 1 to 30 wt. %, inclusive, if present, based on the total weight of the photopolymerizable composition;
d. 0.1 to 5 wt. %, inclusive, of at least one initiator; and
e. an optional inhibitor in an amount of 0.001 to 1 wt. %, inclusive, if present, based on the total weight of the photopolymerizable composition.

In many embodiments, the photopolymerizable composition of the article is vat polymerized, as discussed in detail below.

The shape of the article is not limited, and may comprise a film or a shaped integral article. For instance, a film may readily be prepared by casting the photopolymerizable composition according to the first aspect, then subjecting the cast composition to actinic radiation to polymerize the photopolymerizable composition. In many embodiments, the article comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods. In some embodiments, the article comprises a plurality of layers. In select embodiments, the article comprises an orthodontic article. Orthodontic articles are described in further detail below.

In a third aspect, the present disclosure provides a method of making an article. The method comprises:
(a) providing a photopolymerizable composition comprising a blend of: (i) 30 to 70 wt. %, inclusive, of at least one urethane component; (ii) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (iii) optionally at least one difunctional reactive diluent in an amount of 1 to 30 wt. %, inclusive, if present, based on the total weight of the photopolymerizable composition; (iv) 0.1 to 5 wt. %, inclusive, of at least one initiator; and (v) an optional inhibitor in an amount of 0.001 to 1 wt. %, inclusive, if present; based on the total weight of the photopolymerizable composition;
(b) selectively curing the photopolymerizable composition to form an article; and
(c) optionally curing unpolymerized urethane component and/or reactive diluent remaining after step (b).

In many embodiments, the photopolymerizable composition is cured using actinic radiation comprising UV radiation, e-beam radiation, visible radiation, or a combination thereof. Moreover, the method optionally further comprises postcuring the article using actinic radiation or heat.

In additive manufacturing methods, the method further comprises (d) repeating steps (a) and (b) to form multiple layers and create the article comprising a three dimensional structure prior to step (c). In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall (e.g., floor).

In some embodiments, the method further comprises (e) subjecting the article to heating in an oven, for instance a vacuum oven. Typically, the oven is set at a temperature of 60° C. or higher. A stepwise heating process is optional, such as heating at 60° C., then at 80° C., and then at 100° C. Subjecting the article to heating is often performed to drive off unreacted reactive diluent remaining in the article.

A photopolymerizable composition described herein in a cured state, in some embodiments, can exhibit one or more desired properties. A photopolymerizable composition in a "cured" state can comprise a photopolymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured photopolymerizable composition is at least about 50%, at least about 70%, at least about 80%, or at least about 90% polymerized or crosslinked. A cured photopolymerizable composition can also be between about 10% and about 99% polymerized or crosslinked.

The conformability and durability of a cured article made from the photopolymerizable compositions of the present disclosure can be determined in part by standard tensile, modulus, and/or elongation testing. The photopolymerizable compositions can typically be characterized by at least one of the following parameters after hardening. Advantageously, the elongation at break is typically 25% or greater, 27% or greater, 30% or greater, 32% or greater, 35% or greater, 40% or greater, 45% or greater, 50% or greater, 55% or greater, or 60% or greater; and 200% or less, 100% or less, 90% or less, 80% or less, or 70% or less. Stated another way, the elongation at break of the cured article can range from 25% to 200%. In some embodiments, the elongation at break is at least 30% and no greater than 100%. The ultimate tensile strength is typically 15 MegaPascals (MPa) or greater, 20 MPA or greater, 25 MPa or greater, or 30 MPa or greater, and is typically 80 MPa or less, each as determined according to ASTM D638-10. While the urethane component has the greatest effect on the elongation at break of an article, other components of the photopolymerizable composition also impact the elongation at break, e.g., the length of a linear chain or branch of a reactive diluent tends to be positively correlated to the elongation at break of the final article. The tensile modulus is typically 250 MPa or greater, 500 MPa or greater, 750 MPa or greater, or 1,000 MPa or greater, as determined according to ASTM D638-10. Such elongation properties can be measured, for example, by the methods outlined in ASTM D638-10, using test specimen Type V. The mechanical properties above are particularly well suited for articles that require resiliency and flexibility, along with adequate wear strength and low hygroscopicity.

Photopolymerizable compositions described herein can be mixed by known techniques. In some embodiments, for instance, a method for the preparation of a photopolymerizable composition described herein comprises the steps of mixing all or substantially all of the components of the photopolymerizable composition, heating the mixture, and optionally filtering the heated mixture. Softening the mixture, in some embodiments, is carried out at a temperature of about 50° C. or in a range from about 50° C. to about 85° C. In some embodiments, a photopolymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

Fabricating an Article

Once prepared as set forth above, the photopolymerizable compositions of the present disclosure may be used in myriad additive manufacturing processes to create a variety of articles, including casting a film as noted above. A generalized method 100 for creating three-dimensional articles is illustrated in FIG. 1. Each step in the method will be discussed in greater detail below.

First, in Step 110 the desired photopolymerizable composition (e.g., comprising at least one urethane component, at least one monofunctional reactive diluent, and an initiator) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three dimensional structure (e.g., an orthodontic aligner). Optionally uncured photopolymerizable composition is removed from the article in Step 140, further optionally, the article is subjected to additional curing to polymerize remaining uncured photopolymerizable components in the article in Step 150, and even further optionally, the article is subjected to heat to drive off remaining unreacted reactive diluent in Step 160.

Methods of printing a three dimensional article or object described herein can include forming the article from a plurality of layers of a photopolymerizable composition described herein in a layer-by-layer manner. Further, the layers of a build material composition can be deposited according to an image of the three dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater bead. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, S.C. and the Asiga Pico Plus39, available from Asiga USA, Anaheim Hills, Calif.

Figure 2:
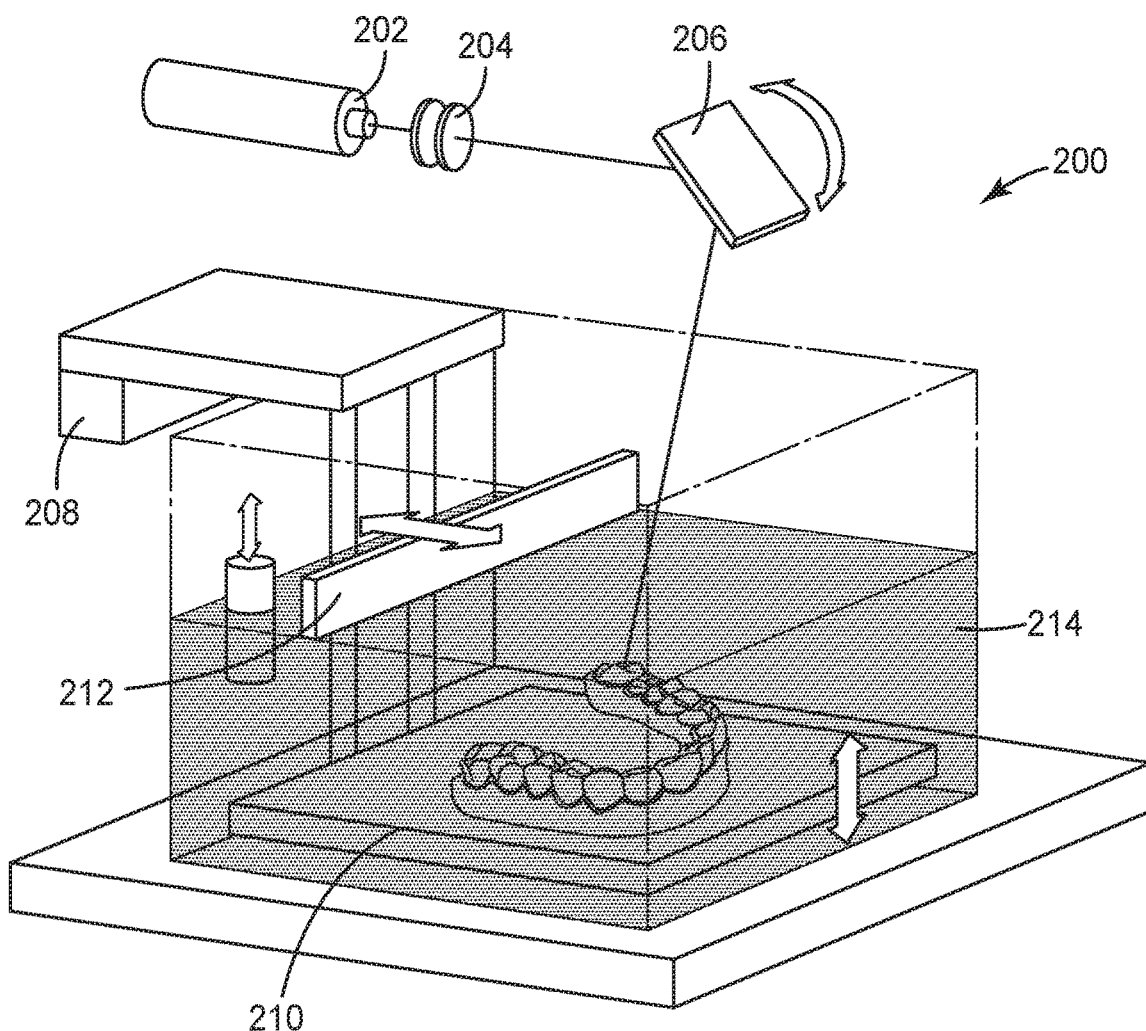
FIG. 2 is a generalized schematic of a stereolithography apparatus.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, Calif.), for instance as described in U.S. Pat. Nos. 9,205,601 and 9,360,757 (both to De Simone et al.).

Figure 5:
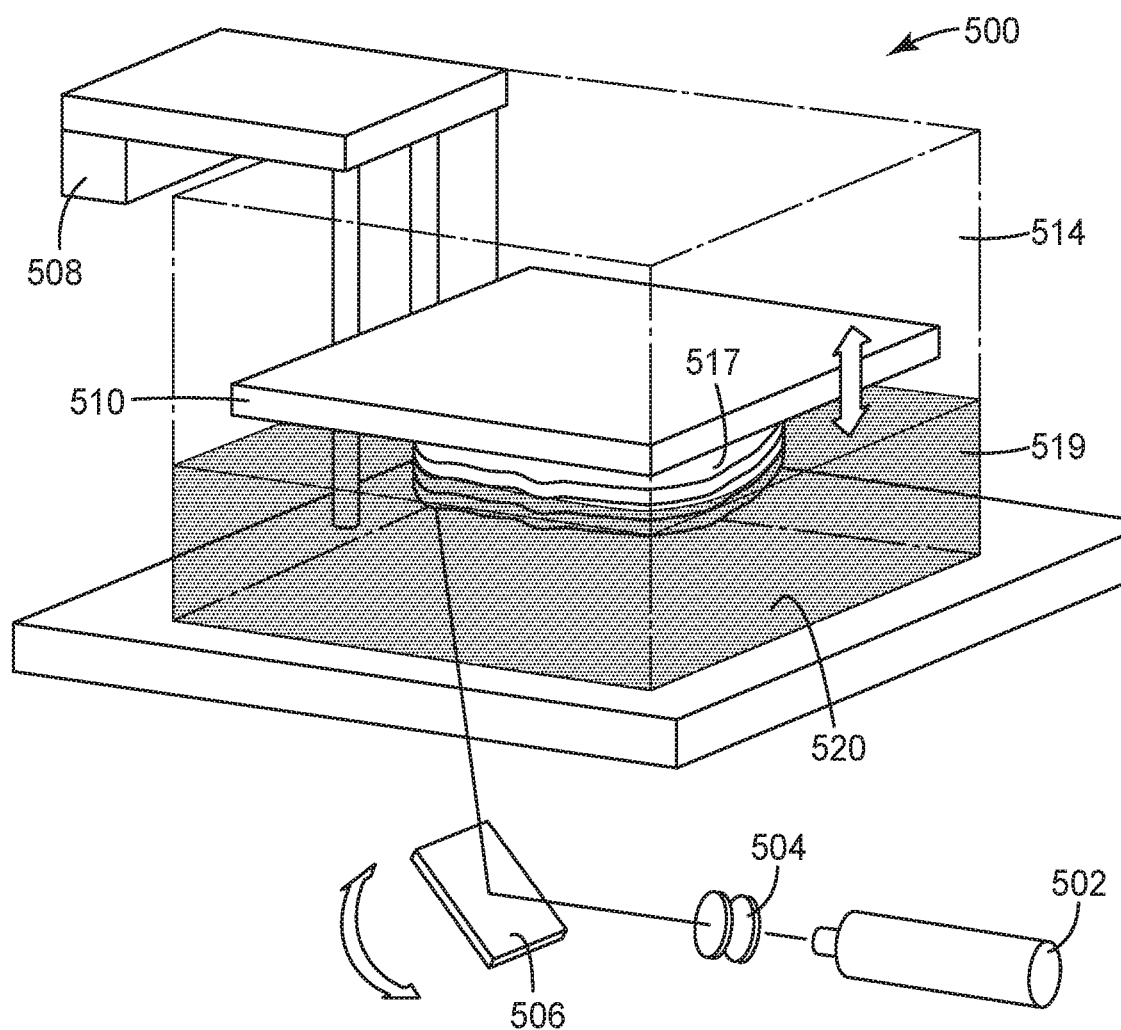
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional postcuring. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to postcuring.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be postcured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the postcure process of Step 150. In general, postcuring improves the mechanical properties and stability of the three-dimensional article relative to the same three-dimensional article that is not postcured. In certain embodiments, the article is also subjected to heat to drive off remaining unreacted reactive diluent in Step 160.

The following describes general methods for creating a clear tray aligner as printed appliance 300. However, other dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

In certain embodiments, the (e.g., orthodontic) article advantageously has a certain equilibrium modulus even after stress relaxation provides a particular maximum amount of stress relaxation. The equilibrium modulus after stress relaxation can be measured by monitoring the stress resulting from a steady strain over time at a specific temperature (e.g., 37° C.) and a specific relative humidity (e.g., 100% relative humidity). In at least certain embodiments, the equilibrium modulus is 100 MPa or greater after 24 hours at 2% strain under 100% relative humidity and 37° C.

Alternatively, the photopolymerizable compositions can be used in other industries, such as aerospace, animation and entertainment, architecture and art, automotive, consumer goods and packaging, education, electronics, hearing aids, sporting goods, jewelry, medical, manufacturing, etc.

Fabricating an Orthodontic Appliance with the Photopolymerizable Compositions

Figure 3:
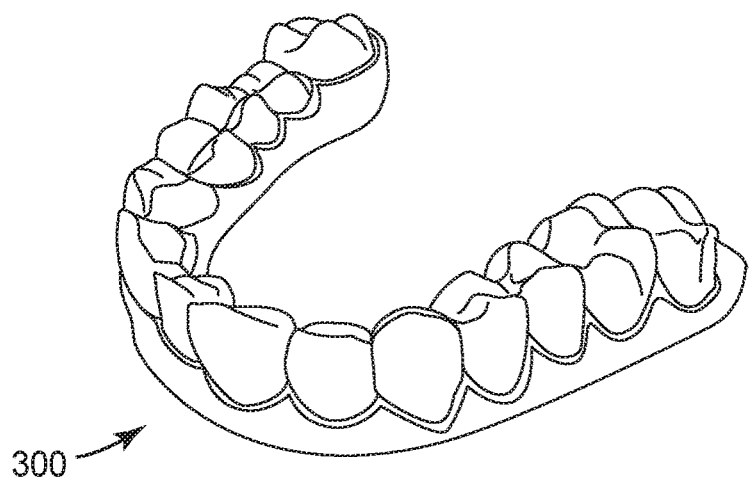
FIG. 3 is an isometric view of a printed clear tray aligner, according to one embodiment of the present disclosure.

One particularly interesting implementation of an article is generally depicted in FIG. 3. The additive manufactured article 300 is a clear tray aligner and is removably positionable over some or all of a patient's teeth. In some embodiments, the appliance 300 is one of a plurality of incremental adjustment appliances. The appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of receptacles may be misaligned as compared to the corresponding tooth of the patient. In this manner, the appliance 300 may be configured to apply rotational and/or translational forces to the corresponding tooth of the patient when the appliance 300 is worn by the patient. In some particular examples, the appliance 300 may be configured to provide only compressive or linear forces. In the same or different examples, the appliance 300 may be configured to apply translational forces to one or more of the teeth within receptacles.

In some embodiments, the shell of the appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. An appliance 300 can accordingly be designed such that any receptacle is shaped to facilitate retention of the tooth in a particular position in order to maintain the current position of the tooth.

Figure 4:
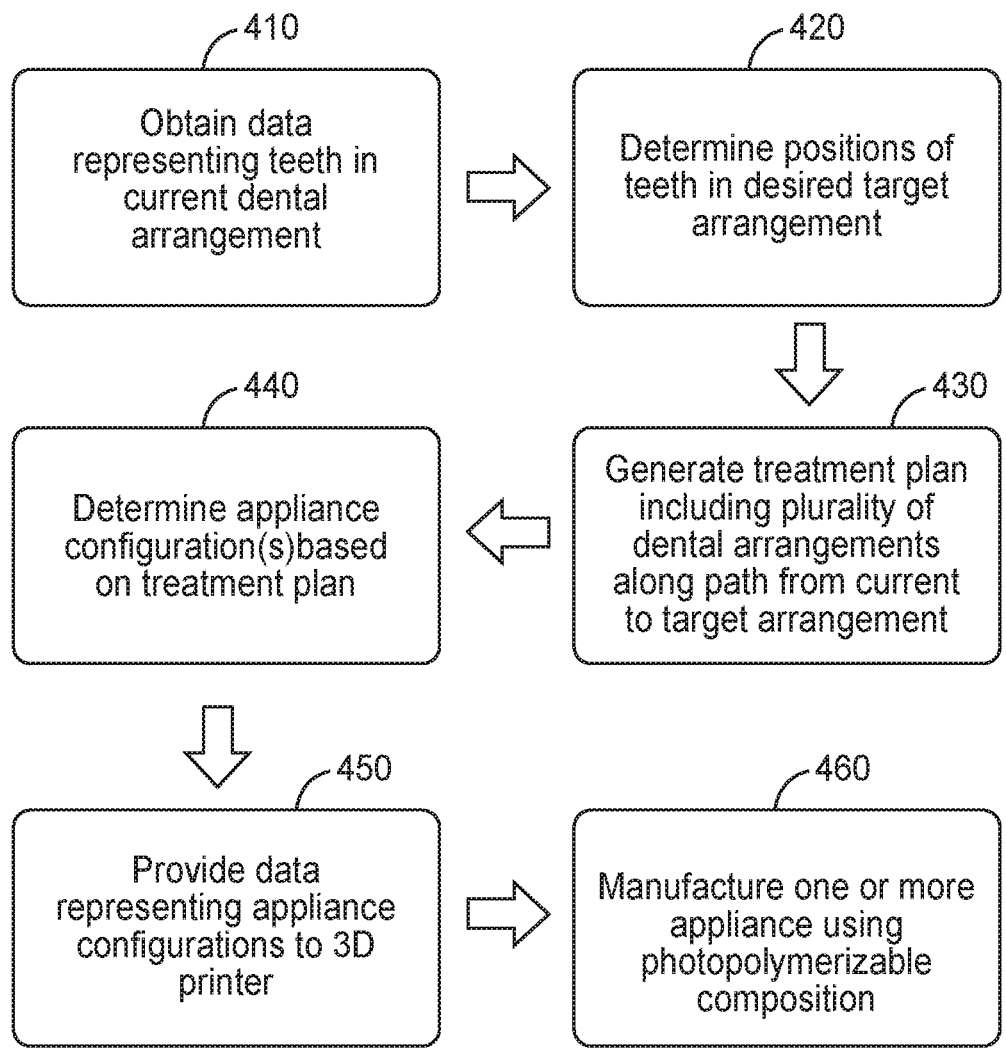
FIG. 4 is a flowchart of a process for manufacturing a printed orthodontic appliance according to the present disclosure.

A method 400 of creating an orthodontic appliance using the photopolymerizable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to an additive manufacturing device (e.g., a 3D printer system) (Step 450). An appliance can be manufactured using a photopolymerizable composition of the present disclosure retained in the additive manufacturing device (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition. In certain embodiments, the article is an orthodontic article. Preferably, the article has an elongation at break of 25% or greater.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In embodiments wherein the article is an orthodontic article, scanning techniques may include, for example, scanning a patient's mouth to customize an orthodontic article for the patient.

Figure 10:
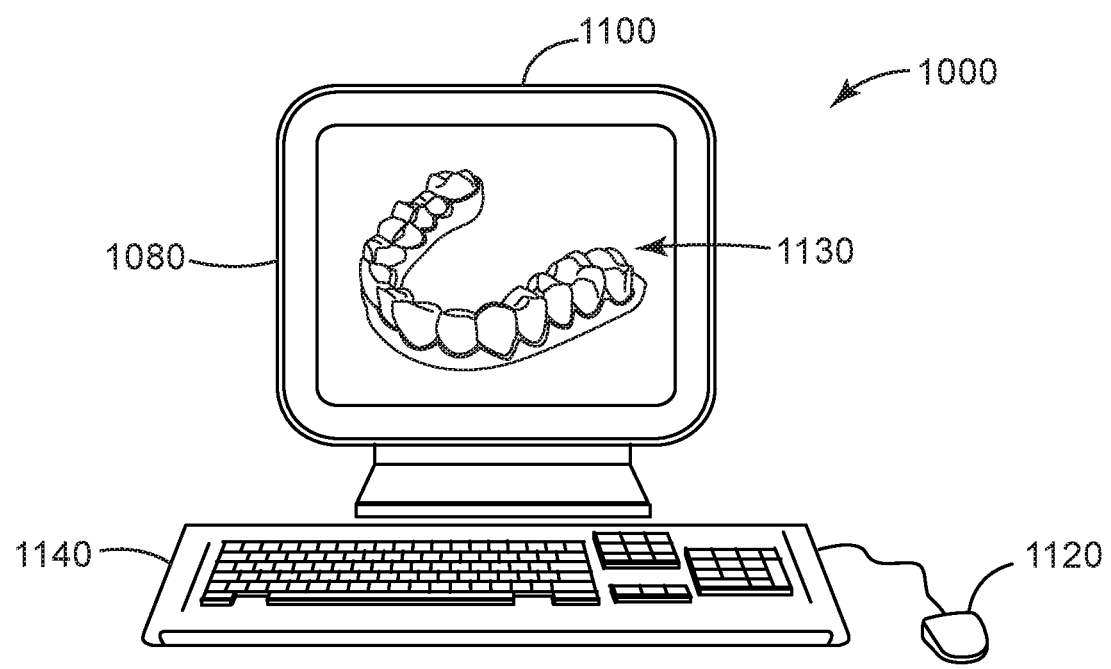
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner 1130 is shown on the display 1100.

Figure 6:
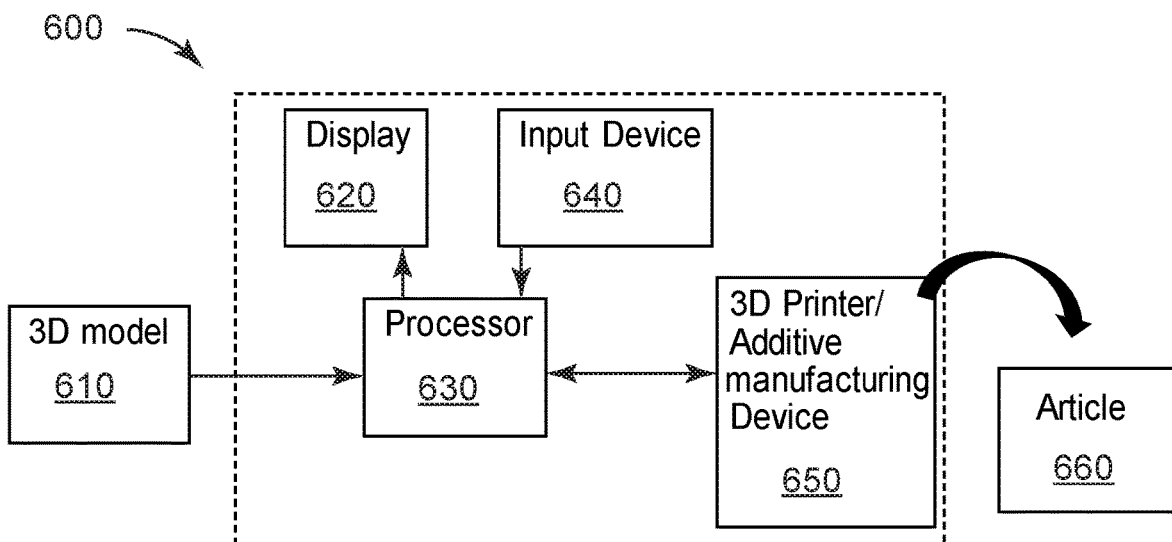
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Figure 7:
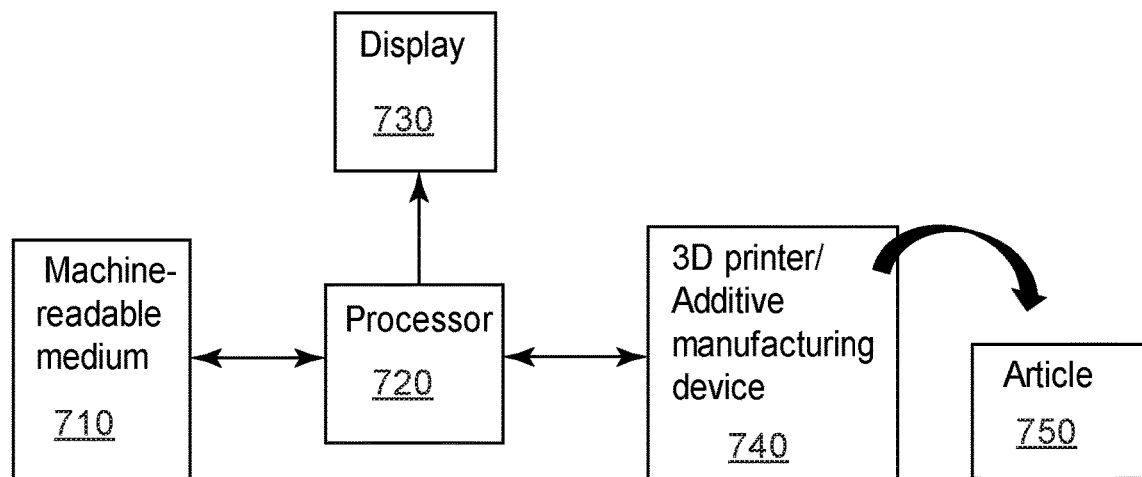
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner 1130 as shown on the display 1100 of FIG. 10) from the machine-readable medium 710.

Figure 8:
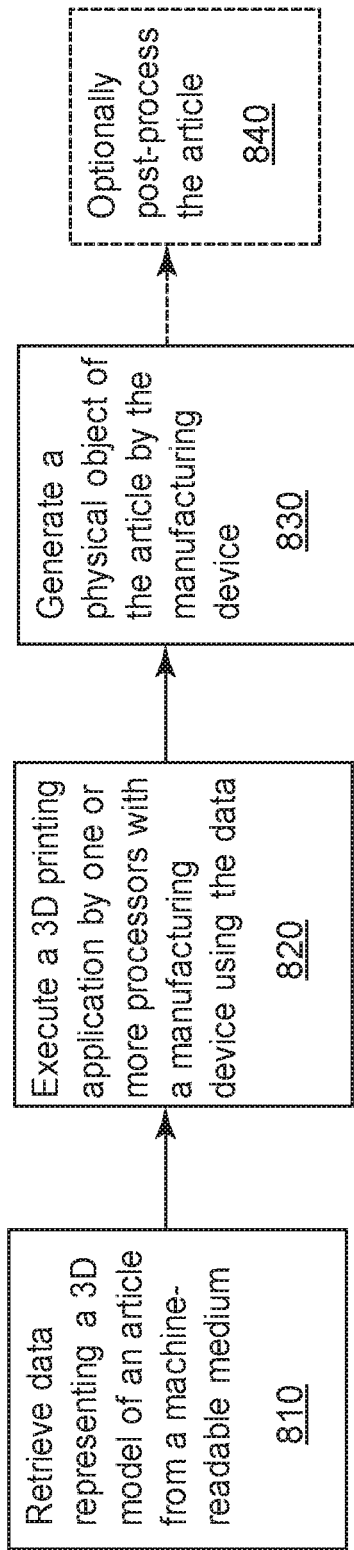
FIG. 8 is a high-level flow chart of an exemplary article manufacturing process.
Figure 9:
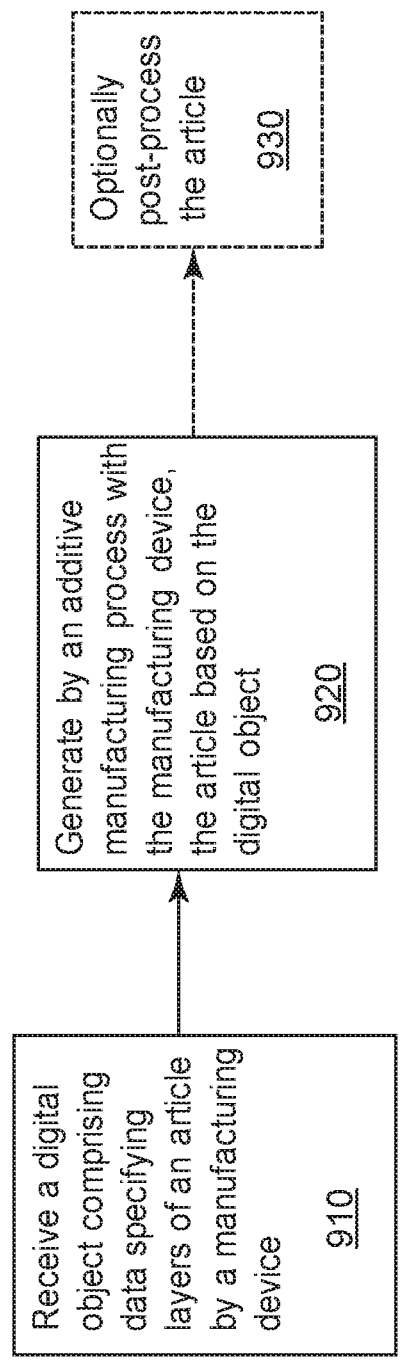
FIG. 9 is a high-level flow chart of an exemplary article additive manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition, the photopolymerizable composition comprising a blend of: (a) 30 to 70 wt. %, inclusive, of at least one urethane component; (b) 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius; (c) optionally at least one difunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition. One or more various optional post-processing steps 840 may be undertaken. Typically, remaining unpolymerized photopolymerizable component may be cured. In certain embodiments, the article comprises an orthodontic article. Preferably, the article exhibits an elongation at break of 25% or greater. Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930, e.g., to cure unpolymerized urethane component and/or reactive diluent remaining in the article. Typically, the manufacturing device selectively cures a photopolymerizable composition to form the article.

Select Embodiments of the Disclosure

Embodiment 1 is a photopolymerizable composition. The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 2 is the photopolymerizable composition of claim 1, wherein the at least one urethane component is present in an amount of 50 to 70 wt. %, inclusive, of the total weight of the photopolymerizable composition.

Embodiment 3 is the photopolymerizable composition of embodiment 1 or embodiment 2, wherein the at least one urethane component includes a high number average molecular weight (Mn) urethane component having one or more urethane functionalities in the backbone of the compound and a number average molecular weight of 1,000 grams per mole (g/mol) or greater, with the proviso that all branches off the backbone of the compound, if present, have a Mn of no more than 200 g/mol.

Embodiment 4 is the photopolymerizable composition of any of embodiments 1 to 3, wherein the at least one urethane oligomer comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof.

Embodiment 5 is the photopolymerizable composition of any of embodiments 1 to 4, wherein the at least one urethane component includes a urethane (meth)acrylate comprising a polyalkylene oxide linking group, a polyamide linking group, or combinations thereof.

Embodiment 6 is the photopolymerizable composition of any of embodiments 1 to 5, wherein the at least one monofunctional reactive diluent is present in an amount of 30 to 50 wt. %, inclusive, of the total weight of the photopolymerizable composition.

Embodiment 7 is the photopolymerizable composition of any of embodiments 1 to 6, wherein the at least one monofunctional reactive diluent includes a compatibilizer present in an amount of at least 30 wt. % of the amount of the at least one urethane component.

Embodiment 8 is the photopolymerizable composition of any of embodiments 1 to 7, wherein the at least one monofunctional reactive diluent further includes at least one monofunctional reactive diluent having a $T_g$ of 25 degrees Celsius or greater.

Embodiment 9 is the photopolymerizable composition of any of embodiments 1 to 8, wherein the at least one monofunctional reactive diluent includes each of at least one monofunctional reactive diluent having a $T_g$ of up to but not including 25 degrees Celsius and at least one monofunctional reactive diluent having a $T_g$ of 25 degrees Celsius or greater.

Embodiment 10 is the photopolymerizable composition of any of embodiments 1 to 9, wherein the at least one monofunctional reactive diluent includes two monofunctional reactive diluents.

Embodiment 11 is the photopolymerizable composition of any of embodiments 1 to 10, wherein the at least one monofunctional reactive diluent includes three monofunctional reactive diluents.

Embodiment 12 is the photopolymerizable composition of embodiment 10, wherein the at least one monofunctional reactive diluent includes one monofunctional reactive diluent having a $T_g$ of up to but not including 25 degrees Celsius and two monofunctional reactive diluents having a $T_g$ of 25 degrees Celsius or greater.

Embodiment 13 is the photopolymerizable composition of embodiment 10, wherein the at least one monofunctional reactive diluent includes two monofunctional reactive diluents having a $T_g$ of up to but not including 25 degrees Celsius and one monofunctional reactive diluent having a $T_g$ of 25 degrees Celsius or greater.

Embodiment 14 is the photopolymerizable composition of any of embodiments 1 to 13, wherein the at least one monofunctional reactive diluent includes a (meth)acrylate, an alkyl (meth)acrylate, a phenoxy (meth)acrylate, a hydroxy alkyl (meth)acrylate, or a combination thereof.

Embodiment 15 is the photopolymerizable composition of any of embodiments 1 to 14, wherein the at least one monofunctional reactive diluent includes phenoxy ethyl methacrylate.

Embodiment 16 is the photopolymerizable composition of embodiment 15, including phenoxy ethyl methacrylate in an amount of 20 to 80 wt. % of the total amount of the at least one monofunctional reactive diluent.

Embodiment 17 is the photopolymerizable composition of any of embodiments 1 to 16, wherein the at least one multifunctional reactive diluent is present in an amount of 5 to 20 wt. %, inclusive, based on the total weight of the photopolymerizable composition.

Embodiment 18 is the photopolymerizable composition of any of embodiments 1 to 17, wherein the at least one multifunctional reactive diluent is present and comprises a polyester methacrylate.

Embodiment 19 is the photopolymerizable composition of any of embodiments 1 to 18, wherein the at least one monofunctional reactive diluent includes a monofunctional reactive diluent exhibiting a hydrophilic-lipophilic balance (HLB) value of less than 10.

Embodiment 20 is the photopolymerizable composition of any of embodiments 1 to 19, further including 0.01 to 1 wt. %, inclusive, of an absorption modifier.

Embodiment 21 is the photopolymerizable composition of any of embodiments 1 to 20, wherein the photopolymerizable composition has a viscosity at a temperature of 25 degrees Celsius of 10 Pa·s or less, as determined using a magnetic bearing rheometer using a 40 mm cone and plate measuring system at a shear rate of 0.1 l/s.

Embodiment 22 is the photopolymerizable composition of any of embodiments 1 to 21, further including at least one filler.

Embodiment 23 is the photopolymerizable composition of any of embodiments 1 to 22, further including at least one filler selected from silica, alumina, zirconia, and discontinuous fibers. Embodiment 24 is the photopolymerizable composition of embodiment 23, wherein the silica includes surface-modified silica nanoparticles.

Embodiment 25 is the photopolymerizable composition of embodiment 22 or embodiment 23, wherein the discontinuous fibers include carbon, ceramic, glass, or combinations thereof.

Embodiment 26 is the photopolymerizable composition of any of embodiments 1 to 25, wherein the at least one initiator includes a first photoinitiator.

Embodiment 27 is the photopolymerizable composition of embodiment 26, wherein the at least one initiator further includes a second photoinitiator.

Embodiment 28 is the photopolymerizable composition of embodiment 26 or embodiment 27, wherein the at least one initiator further includes a thermal initiator.

Embodiment 29 is the photopolymerizable composition of any of embodiments 1 to 28, wherein the at least one monofunctional reactive diluent is present in the form a prepolymer.

Embodiment 30 is the photopolymerizable composition of embodiment 29, wherein the prepolymer includes polymerization of up to 10%, up to 15%, or up to 20% of the functional groups of the at least one monofunctional reactive diluent.

Embodiment 31 is the photopolymerizable composition of any of embodiments 1 to 30, wherein the at least one urethane component includes at least one pendant group comprising a photoinitiator.

Embodiment 32 is an article including a reaction product of a photopolymerizable composition. The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 33 is the article of embodiment 32, wherein the article comprises a plurality of layers.

Embodiment 34 is the article of embodiment 32 or embodiment 33, including a film or a shaped integral article.

Embodiment 35 is the article of any of embodiments 32 to 34, including an orthodontic article.

Embodiment 36 is the article of any of embodiments 32 to 35, including one or more channels, one or more undercuts, one or more perforations, or combinations thereof.

Embodiment 37 is the article of any of embodiments 32 to 36, exhibiting an elongation at break of 25% or greater.

Embodiment 38 is the article of any of embodiments 32 to 37, exhibiting an elongation at break of 40% or greater.

Embodiment 39 is the article of any of embodiments 32 to 38, exhibiting a tensile strength of 20 MegaPascals (MPa) or greater, as determined according to ASTM D638-10.

Embodiment 40 is the article of any of embodiments 32 to 39, exhibiting a tensile strength of 30 MPa or greater, as determined according to ASTM D638-10.

Embodiment 41 is the article of any of embodiments 32 to 40, exhibiting a modulus of 500 MPa or greater, as determined according to ASTM D638-10.

Embodiment 42 is the article of any of embodiments 32 to 41, exhibiting a modulus of 1,000 MPa or greater, as determined according to ASTM D638-10.

Embodiment 43 is the article of any of embodiments 32 to 42, wherein the at least one urethane component is present in an amount of 50 to 70 wt. %, inclusive, of the total weight of the photopolymerizable composition.

Embodiment 44 is the article of any of embodiments 32 to 43, wherein the at least one urethane component includes a high number average molecular weight (Mn) urethane component having one or more urethane functionalities in the backbone of the compound and a number average molecular weight of 1,000 grams per mole (g/mol) or greater, with the proviso that all branches off the backbone of the compound, if present, have a Mn of no more than 200 g/mol.

Embodiment 45 is the article of any of embodiments 32 to 44, wherein the at least one urethane oligomer comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof.

Embodiment 46 is the article of any of embodiments 32 to 45, wherein the at least one urethane component includes a urethane (meth)acrylate comprising a polyalkylene oxide linking group, a polyamide linking group, or combinations thereof.

Embodiment 47 is the article of any of embodiments 32 to 46, wherein the at least one monofunctional reactive diluent is present in an amount of 30 to 50 wt. %, inclusive, of the total weight of the photopolymerizable composition.

Embodiment 48 is the article of any of embodiments 32 to 47, wherein the at least one monofunctional reactive diluent includes a compatibilizer present in an amount of at least 30 wt. % of the amount of the at least one urethane component.

Embodiment 49 is the article of any of embodiments 32 to 48, wherein the at least one monofunctional reactive diluent further includes at least one monofunctional reactive diluent having a $T_g$ of 25 degrees Celsius or greater.

Embodiment 50 is the article of any of embodiments 32 to 49, wherein the at least one monofunctional reactive diluent includes each of at least one monofunctional reactive diluent having a $T_g$ of up to but not including 25 degrees Celsius and at least one monofunctional reactive diluent having a $T_g$ of 25 degrees Celsius or greater.

Embodiment 51 is the article of any of embodiments 32 to 50, wherein the at least one monofunctional reactive diluent includes two monofunctional reactive diluents.

Embodiment 52 is the article of any of embodiments 32 to 51, wherein the at least one monofunctional reactive diluent includes three monofunctional reactive diluents.

Embodiment 53 is the article of embodiment 52, wherein the at least one monofunctional reactive diluent includes one monofunctional reactive diluent having a $T_g$ of up to but not including 25 degrees Celsius and two monofunctional reactive diluents having a $T_g$ of 25 degrees Celsius or greater.

Embodiment 54 is the article of embodiment 52, wherein the at least one monofunctional reactive diluent includes two monofunctional reactive diluents having a $T_g$ of up to but not including 25 degrees Celsius and one monofunctional reactive diluent having a $T_g$ of 25 degrees Celsius or greater.

Embodiment 55 is the article of any of embodiments 32 to 54, wherein the at least one monofunctional reactive diluent includes a (meth)acrylate, an alkyl (meth)acrylate, a phenoxy (meth)acrylate, a hydroxy alkyl (meth)acrylate, or a combination thereof.

Embodiment 56 is the article of any of embodiments 32 to 55, wherein the at least one monofunctional reactive diluent includes phenoxy ethyl methacrylate.

Embodiment 57 is the article of embodiment 56, comprising phenoxy ethyl methacrylate in an amount of 20 to 80 wt. % of the total amount of the at least one monofunctional reactive diluent.

Embodiment 58 is the article of any of embodiments 32 to 57, wherein the at least one multifunctional reactive diluent is present in an amount of 5 to 20 wt. %, inclusive, based on the total weight of the photopolymerizable composition.

Embodiment 59 is the article of any of embodiments 32 to 58, wherein the at least one multifunctional reactive diluent is present and comprises a polyester methacrylate.

Embodiment 60 is the article of any of embodiments 32 to 58, wherein the at least one monofunctional reactive diluent comprises a monofunctional reactive diluent exhibiting a HLB value of less than 10.

Embodiment 61 is the article of any of embodiments 32 to 60, further including 0.01 to 1 wt. %, inclusive, of an absorption modifier.

Embodiment 62 is the article of any of embodiments 32 to 61, wherein the photopolymerizable composition has a viscosity at a temperature of 25 degrees Celsius of 10 Pa·s or less, as determined using a magnetic bearing rheometer using a 40 mm cone and plate measuring system at a shear rate of 0.1 1/s.

Embodiment 63 is the article of any of embodiments 32 to 62, further including at least one filler.

Embodiment 64 is the article of any of embodiments 32 to 63, further including at least one filler selected from silica, alumina, zirconia, and discontinuous fibers.

Embodiment 65 is the article of embodiment 64, wherein the silica comprises surface-modified silica nanoparticles.

Embodiment 66 is the article of embodiment 64 or embodiment 65, wherein the discontinuous fibers include carbon, ceramic, glass, or combinations thereof.

Embodiment 67 is the article of any of embodiments 32 to 66, wherein the at least one initiator includes a first photoinitiator.

Embodiment 68 is the article of embodiment 67, wherein the at least one initiator further includes a second photoinitiator.

Embodiment 69 is the article of embodiment 67 or embodiment 68, wherein the at least one initiator further includes a thermal initiator.

Embodiment 70 is article of any of embodiments 32 to 69, wherein the at least one urethane component includes at least one pendant group comprising a photoinitiator.

Embodiment 71 is a method of making an article is provided. The method includes (a) providing a photopolymerizable composition and (b) selectively curing the photopolymerizable composition to form an article. Optionally, the method further includes (c) curing unpolymerized urethane component and/or reactive diluent remaining after step (b). The photopolymerizable composition includes a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 72 is the method of embodiment 71, further including (d) repeating steps (a) and (b) to form multiple layers and create the article having a three dimensional structure prior to step (c).

Embodiment 73 is the method of embodiment 71 or embodiment 72, further including (e) subjecting the article to heating in an oven.

Embodiment 74 is the method of embodiment 73, wherein the oven is set at a temperature of 60 degrees Celsius or higher.

Embodiment 75 is the method of embodiment 73 or claim 74, wherein the article is subjected to stepwise heating at 60 degrees Celsius, 80 degrees C., and then 100 degrees Celsius.

Embodiment 76 is the method of any of embodiments 73 to 75, wherein the oven comprises a vacuum oven.

Embodiment 77 is the method of any of embodiments 71 to 76, wherein the photopolymerizable composition is cured using actinic radiation including UV radiation, e-beam radiation, visible radiation, or a combination thereof.

Embodiment 78 is the method of embodiment 77, wherein the radiation is directed through a wall of a container holding the photopolymerizable composition.

Embodiment 79 is the method of any of embodiments 71 to 78, wherein the photopolymerizable composition is cured through a floor of a container holding the photopolymerizable composition.

Embodiment 80 is the method of any embodiments 71 to 79, further including postcuring the article using actinic radiation or heat.

Embodiment 81 is the method of any of embodiments 71 to 80, wherein the method includes vat polymerization of the photopolymerizable composition.

Embodiment 82 is the method of any of embodiments 71 to 81, wherein the at least one initiator includes a first photoinitiator.

Embodiment 83 is the method of embodiment 82, wherein the at least one initiator further includes a second photoinitiator.

Embodiment 84 is the method of embodiment 82 or claim 83, wherein the at least one initiator further includes a thermal initiator.

Embodiment 85 is the method of any of embodiments 71 to 84, wherein the at least one monofunctional reactive diluent is present in the form a prepolymer.

Embodiment 86 is the photopolymerizable composition of embodiment 85, wherein the prepolymer includes polymerization of up to 10%, up to 15%, or up to 20% of the functional groups of the at least one monofunctional reactive diluent.

Embodiment 87 is the photopolymerizable composition of any of embodiments 71 to 86, wherein the at least one urethane component includes at least one pendant group comprising a photoinitiator.

Embodiment 88 is a non-transitory machine readable medium. The non-transitory machine readable medium has data representing a three-dimensional model of an article, when accessed by one or more processors interfacing with a 3D printer, causes the 3D printer to create an article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 89 is a method. The method includes (a) retrieving, from a non-transitory machine readable medium, data representing a 3D model of an article; (b) executing, by one or more processors, a 3D printing application interfacing with a manufacturing device using the data; and (c) generating, by the manufacturing device, a physical object of the article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 90 is an article generated using the method of embodiment 89.

Embodiment 91 is the article of embodiment 90, wherein the article includes an orthodontic article.

Embodiment 92 is the article of embodiment 90 or embodiment 91, exhibiting an elongation at break of 25% or greater.

Embodiment 93 is a method. The method includes (a) receiving, by a manufacturing device having one or more processors, a digital object comprising data specifying a plurality of layers of an article; and (b) generating, with the manufacturing device by an additive manufacturing process, the article based on the digital object. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

Embodiment 94 is the method of embodiment 93, wherein the manufacturing device selectively cures a photopolymerizable composition to form an article.

Embodiment 95 is the method of embodiment 94, further including curing unpolymerized urethane component and/or reactive diluent, remaining in the article.

Embodiment 96 is the method of any of embodiments 93 to 95, wherein the article includes an orthodontic article.

Embodiment 97 is the method of any of embodiments 93 to 96, wherein the article exhibits an elongation at break of 25% or greater.

Embodiment 98 is a system. The system includes (a) a display that displays a 3D model of an article and (b) one or more processors that, in response to the 3D model selected by a user, cause a 3D printer to create a physical object of an article. The article includes a reaction product of a photopolymerizable composition including a blend of (a) 30 to 70 wt. %, inclusive, of at least one urethane component and (b) 25 to 70 wt. %, inclusive, of at least one monofunctional reactive diluent. The at least one monofunctional reactive diluent includes at least one monofunctional reactive diluent having a $T_g$ of up to but not including 25 degrees Celsius. The photopolymerizable composition further includes (c) optionally at least one multifunctional reactive diluent in an amount of 1 to 30 wt. %, inclusive, if present, based on the total weight of the photopolymerizable composition; (d) 0.1 to 5 wt. %, inclusive, of at least one initiator; and (e) an optional inhibitor in an amount of 0.001 to 1 wt. %, inclusive, if present, based on the total weight of the photopolymerizable composition.

EXAMPLES

Objects and advantages of this disclosure are further illustrated by the following examples, but the particular materials and amounts thereof recited in these examples, as well as other conditions and details, should not be construed to unduly limit this disclosure.

TABLE 1A

| | Materials. | | | |
|---|---|---|---|---|
| | Description | Source | Tg (° C.) | Functionality |
| | Crosslinking components: | | | |
| Exothane 108 | Urethane (meth)acrylate oligomer | Esstech Inc, (Essington, PA, USA) | — | 2 |
| Exothane 10 | Urethane (meth)acrylate oligomer | Esstech Inc, (Essington, PA, USA) | — | 2 |
| H1188 | Polyester Methacrylate | Designer Molecules Inc, (San Diego, CA, USA) | — | 2 |
| | Monofunctional Reactive Diluents: | | | |
| EHMA | Ethyl hexyl methacrylate | Alfa Aesar, (Haverhill, MA, USA) | −10 | 1 |

TABLE 1A-continued

Materials.

| | Description | Source | Tg (° C.) | Functionality |
|---|---|---|---|---|
| PEMA | Phenoxy Ethyl Methacrylate, SR340 | Sartomer (Exton, PA, USA) | 54 | 1 |
| IBoMA | Isobornyl Methacrylate | Sartomer (Exton, PA) | 94 | 1 |
| HEMA | Hydroxyethyl Methacrylate | Esstech Inc (Essington, PA, USA) | 57 | 1 |
| IBuMA | Isobutyl Methacrylate | TCI America, (Portland OR, USA) | 20 | 1 |
| | | Additives: | | |
| BHT | 2,6-Di-tert-butyl-4-methyl-phenol | Fluka Analytical (St. Louis, MO) | — | — |
| TINOPAL OB | 2,5-Thiophenediylbis(5-tert-butyl-1,3-benzoxazole) (optical brightener) | BASF, Wyandotte, MI | — | — |
| IRGAGURE TPO | 2,4,6-Trimethyl-benzoyldiphenylphosphine oxide (photoinitiator) | BASF (Wyandotte, MI) | — | — |

Unless otherwise noted, all printed Examples were printed on an Asiga PicoPlus39, a vat polymerization 3D printer available from Asiga USA, Anaheim Hills, Calif.

Measurement of HLB Values of the Monomer

HLB was obtained by the Griffin's method (See Griffin W C:"Calculation of HLB values of Non-ionic surfactants," Journal of the Society of Cosmetic Chemists 5 (1954):259). The computations were conducted utilizing the software program Molecular Modeling Pro Plus from Norgwyn Montgomery Software, Inc. (North Wales, Pa.).

TABLE 1B

Hydrophilic-Lipophilic Balance (HLB) Values

| Compound | Molecular Weight | HLB |
|---|---|---|
| 2-Ethyl Hexyl Methacrylate | | 3.39971 |
| Hydroxyethyl Methacrylate | | 12.4469 |
| Isobutylmethacrylate | | 4.2239 |
| Isobornyl methacrylate | | 1.93492 |
| Phenoxyethyl methacrylate | | 5.58884 |
| Exothane 10 | | 13.764 |
| H1188 | | 5.32931 |
| U847 | | 4.94337 |

Example 1

Preparation of Prepolymer Solution

Prepolymerization to make syrup (S1) was carried out by mixing 99.95 parts free radical monomer(s) (IBuMA/EHMA/PEMA=1:1:1) with 0.05 parts of free radical initiator, (Irgacure TPO). The mixture was continuously stirred using a magnetic stirrer and degassed by bubbling nitrogen through the solution for at least five minutes. The mixture was then exposed to radiation from a blacklight for about 3 minutes. The reaction was allowed to go to about 10-15% acrylate conversion.

Example 2

Preparation of Oligomer Solution with Pendant Photoinitiator

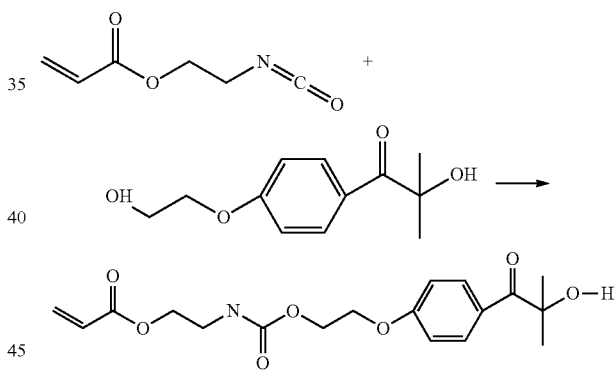

A preparation of PIEA was produced as the product of Irgacure 2959 and 2-isocyanatoethylacrylate (IEA), according to the chemical reaction above. Irgacure 2959 (50.29 g, 224.3 mmol) was dissolved in acetone (150 mL, GFS Chemicals Inc., Powell, Ohio, USA). Di-n-butyltin dilaurate (0.5 g, 0.8 mmol, Alfa Aesar, Tewksbury, Mass., 01876, USA) and BHT (0.2 g, 0.9 mmol) were added, followed by the incremental addition of 2-isocyanatoethyl acrylate (IEA, 3015 g, 213.6 mmol, Show Denko America Inc., New York, N.Y., USA), over 20 minutes with continuous stirring. Samples were taken and the IR spectrum was recorded. After 2-hour reaction time, NCO band (~2200-2500 cm-1) disappeared indicating reaction completion. The solvent was removed in a rotary evaporator followed by further drying under vacuum to give a hazy viscous liquid. The reaction yield was 99.7%.

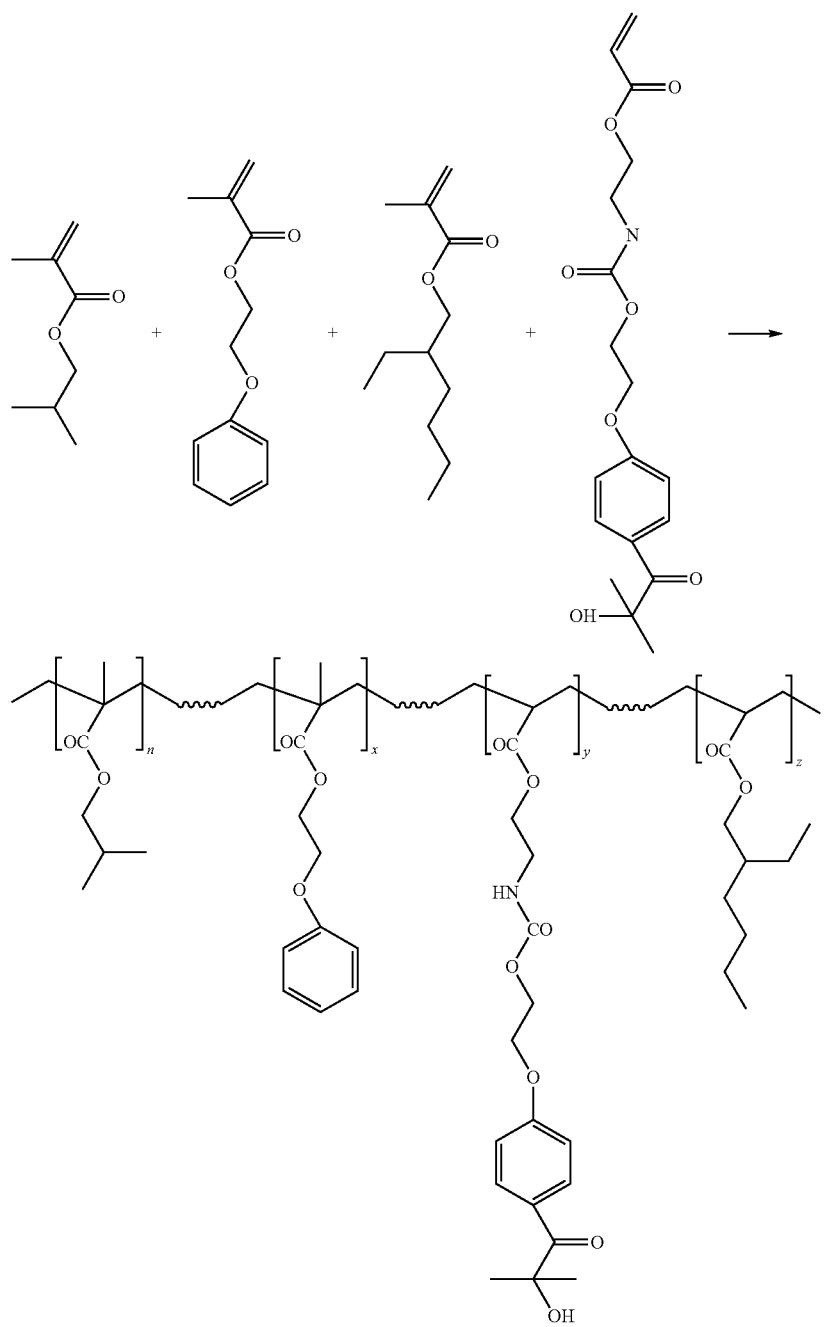

A photo-initiator-carrying polymer (PP1) was prepared per the chemical reaction above. Isobutylmethacrylate (10 g, 70,32 mmol, TCI America, Portland, Oreg., USA), 2-phenoxyethyl methacrylate (PEMA) (10.47 g, 50.77 mmol, Sartomer Americas, Exton, Pa. USA), 2-ethyhexyl methacrylate (10.65 g, 53.71 mmol, TCI America), and PIEA (10.56 g, 28.9 mmol, an adduct of 2-isocyanatoethyl acrylate and Irgacure-2959) were dissolved in isopropyl alcohol (75 mL, GFS Chemicals Inc., Powell, Ohio, USA) in a 250 mL 3-neck flask equipped with an stirring bar, a condenser, a thermocouple and a stream of N2 bubbling into the solution. 2,2'-Azobis(2-methylpropionitrile) ((AIBN), 0.25 g, 1.5 mmol, Sigma Aldrich, St Louis, Mo., USA) was added. After bubbling N2 through the solution for 15 minutes, the heat was raised to 65° C. and stirred overnight. The next day, the heat was turned off and the solution was allowed to cool to room temperature. The solvent was decanted off the product to obtain a moist product, which was then dried under vacuum to give a sticky semi-solid.

Example 3

Preparation of Nanofilled Exothane 10

400.0 grams of NALCO 2327 (NALCO, Naperville, Ill.), a 20 nm silica aqueous nanodispersion, was placed in a 32 ounce clear glass jar. The mixture was agitated on a stir plate with a TEFLON coated stir bar. 450.0 grams of 1-methoxy-2-propanol (Dow, Midland, Mich.) was slowly added to the jar. This was followed by addition of 11.00 grams of 3-methacryloxypropyltrimethoxysilane (Gelest, Morrisville, Pa.) and 8.39 grams of 3-cyanopropyltrimethoxysilane (Gelest, Morrisville, Pa.) to the jar. The nanodispersion in the jar was then mixed for an additional 20 minutes. The stir bar was removed from the jar, and the jar was then transferred to a solvent-rated oven at 80° C. for 24 hours. The nanodispersion was then removed from the oven and allowed to cool to room temperature. The nanodispersion was then transferred to a 2 liter single neck flask round bottom flask. An amount of 330 grams of 1-methoxy-2-propanol was added to the flask. The flask was sealed and the nanodispersion was vigorously agitated to form a homogenous mixture. The flask was then attached to a ROTOVAP, and a solvent exchange was performed to remove water and create a solvent-based nanodispersion of ~41 weight percent solids in 1-methoxy-2-propanol. An amount of 36.5 g of surface treated nanosilica solution was mixed with 30 g of Exothane 10. The mixture was heated in a ROTOVAP at 50° C. under continuous vacuum for 2 hours to remove the solvent. The final nanofilled Exothane 10 mixture (NP1) had 33.33 wt % of silica nanoparticles.

Example 4

Preparation of Formulated Resins

Resins were prepared according to the formulations listed in Tables 2A-2D below, by roller mixing the components overnight to ensure thorough mixing.

TABLE 2A

Resin Formulations (grams)

| Example | CE-1 | CE-2 | CE-3 | CE-4 | E-1 | E-2 | E-3 |
|---|---|---|---|---|---|---|---|
| Exothane 108 | — | — | — | — | — | — | — |
| Exothane 10 | 80 | 20 | — | 50 | 50 | 50 | 50 |
| H1188 | — | — | 50 | — | — | — | — |
| IBuMA | 6.67 | 26.67 | 16.67 | — | 16.7 | 16.7 | 16.7 |
| EHMA | 6.67 | 26.67 | 16.67 | 15 | 16.7 | 16.7 | 16.7 |
| IBoMA | — | — | — | 30 | — | — | 4.7 |
| PEMA | 6.67 | 26.67 | 16.67 | 5 | — | 16.7 | 12.5 |
| HEMA | — | — | — | — | 16.7 | — | — |
| IRGACURE TPO | 2 | 2 | 2 | 2 | 2 | 2 | 2 |
| BHT | 0.025 | 0.025 | 0.025 | 0.25 | 0.025 | 0.025 | 0.025 |

TABLE 2B

Resin Formulations (grams)

| Example | E-4 | E-5 | E-6 | E-7 | E-8 |
|---|---|---|---|---|---|
| Exothane 108 | 14.96 | 15.75 | 15.75 | — | — |
| Exothane 10 | 34.89 | 47.25 | 47.25 | 37.5 | 63 |
| Other ingredient | 15 (NP1) | — | — | — | — |
| H1188 | — | — | 10 | 10 | — |
| U847 | — | — | — | 5 | — |
| IBuMA | — | — | — | — | — |
| EHMA | 8.5 | 9 | 9 | 10 | 10.8 |
| IBoMA | 9.5 | 10 | — | — | 10 |
| PEMA | 17.1 | 18 | 18 | 37.5 | 16.2 |
| IRGACURE TPO | 2 | 2 | 2 | 2 | 2 |
| BHT | 0.025 | 0.025 | 0.025 | 0.025 | 0.025 |

TABLE 2C

Resin Formulations (grams) EXAMPLES E-9-E13

| Example | E-9 | E-10 | E-11 | E12 | E13 |
|---|---|---|---|---|---|
| Exothane 108 | — | — | — | — | 30 |
| Exothane 10 | 70 | 40 | 50 | 30 | — |
| H1188 | — | 10 | — | 10 | 20 |
| U847 | — | — | — | 10 | — |
| IBuMA | — | — | — | 16.7 | 15 |
| EHMA | 12 | 15 | 10 | 16.7 | 15 |
| IBoMA | — | — | — | — | — |
| PEMA | 18 | 35 | 40 | 16.7 | 15 |
| HEMA | — | — | — | — | — |
| IRGACURE TPO | 2 | 2 | 2 | 2 | 2 |
| BHT | 0.025 | 0.025 | 0.025 | 0.025 | 0.025 |

TABLE 2D

| Resin Formulations (grams) EXAMPLES E-14-E-16 | | | |
|---|---|---|---|
| Example | E-14 | E-15 | E-16 |
| Exothane 108 | — | — | — |
| Exothane 10 | 40 | 40 | 50 |
| H1188 | 10 | 10 | — |
| Special ingredient | — | 50 (S1) | 10 (PP1) |
| IBuMA | 16.7 | — | 13.33 |
| EHMA | 16.7 | — | 13.33 |
| IBoMA | — | — | — |
| PEMA | 16.7 | — | 13.33 |
| HEMA | — | — | — |
| IRGACURE TPO | 2 | 2 | 2 |
| BHT | 0.025 | 0.025 | 0.025 |

Example 5

Viscosity of the Resins

Absolute (e.g., dynamic) viscosities of the example resins were measured using a TA Instruments AR-G2 magnetic bearing rheometer using a 40 millimeter cone and plate measuring system at 40° C. at a shear rate of 0.1 1/s. Two replicates were measured and the average value was reported as the viscosity, in Pa·s, in Table 3 below.

TABLE 3

| Viscosities of Example resins in Pa · s. | |
|---|---|
| Sample ID | Viscosity (Pa · s) |
| CE-1 | Too viscous to be printable |
| CE-2 | 0.176 |
| CE-3 | 0.275 |
| CE-4 | Not compatible, phase separated |
| E-1 | 0.181 |
| E-2 | 0.152 |
| E-3 | 0.298 |
| E-4 | 2.33 |
| E-5 | 1.478 |
| E-6 | 3.39 |
| E-7 | 0.331 |
| E-8 | 1.865 |
| E-9 | 2.766 |
| E-10 | 0.251 |
| E-11 | 0.410 |
| E-12 | 0.167 |
| E-13 | 0.215 |
| E-14 | 0.277 |
| E-15 | 0.508 |
| E-16 | 0.163 |

Example 6

Physical Properties of Polymers from Cast Resin Formulations

The Example 1 (E-1) formulation shown in Table 2A was mixed in a glass jar. The E-1 mixture was placed on a rolling mixer to make a homogenous mixture. The mixture was degassed and speed mixed in THINKY planetary mixer (Thinky Corporation, Tokyo, Japan), at 2000 rpm for 90 seconds under vacuum. The mixture was then poured in a silicone dogbone mold (Type V mold, ASTM D638-10). For modulus measurements, a rectangular piece of dimensions (12 mm×63.5 mm×1 mm) was cast in a silicone mold. The filled mold was placed between two glass plates and cured in Asiga Pico Flash post-curing device for 15 minutes. The sample was demolded and cured for another 15 minutes in the chamber. The dogbones were kept in a vacuum oven at 100° C. overnight to remove any residual unreacted monomer. These dogbones were tested on an Insight MTS with 5 kN load cell at the rate of 5 mm/minute. Five replicate samples were tested, and the average and standard deviation are reported. The tensile strength was determined according to ASTM D638-10 and shown in Table 4 below. Elongation at break was determined from the crosshead movement of the grips and the samples were not strain gauged. For modulus, the modulus rectangular samples were pulled in tension at the rate of 1 mm/min until 5% strain was achieved. The initial slope of the stress-strain curve is reported as the modulus of the part.

Subsequent examples, E-2-E-15 and CE-1-CE-3, were made by the same method (the formulations for these examples are summarized in Tables 2A-2D above) and tested. For E-16 an additional UV cure for 10 mins was done in presence of germicidal lamp (GE G30T8, 30 W bulb). The test results of the cast samples are summarized in Table 4 below.

TABLE 4

| Tensile strength (MPa), Tensile Modulus (MPa) and Elongation at break (%) of Cast Formulations. | | | |
|---|---|---|---|
| Sample ID | Tensile Strength (Std Dev) | Tensile Modulus (Std Dev) | Crosshead Elongation at Break (Std Dev) |
| CE-1 | 47.8 (0.38) | 1122.8 | 48.2 (30.1) |
| CE-2 | 10.9 (0.8) | — | 188.9 (15.2) |
| CE-3 | 59.1 (4.6) | — | 7.7 (1) |
| CE-4 | Phase separated | — | — |
| E-1 | 48.4 (0.58) | | 62.2 (27.2) |
| E-2 | 32.3 (1) | 991.4 | 101 (20.5) |
| E-3 | 35.8 (0.9) | | 55.2 (25.6) |
| E-4 | 37.7 (1) | 1374.9 | 97.5 (17.9) |
| E-5 5 wt % nanofilled | 37.1 (0.4) | 1169.2 | 99.6 (19.5) |
| E-6 | 39.7 (0.6) | 1288.4 | 62 (13.3) |
| E-7 | 46.0 (1.3) | 1359.8 | 51 (13.5) |
| E-8 | 41.4 (2.4) | 1306.9 | 42.2 (27.3) |
| E-9 | 41.9 (0.7) | 1323 | 74.3 (25.2) |
| E-10 | 45.1 (0.6) | 1164.7 | 47.5 (13.6) |
| E-11 | 39.1 (1.1) | 1254.3 | 60.3 (43.3) |
| E-12 | 33.2 (2.1) | 823.4 | 50.3 (16.3) |
| E-13 | 30.6 (1.9) | 976.4 | 44.1 (10.4) |
| E-14 | 40.3 (0.6) | 1214.2 | 47.5 (12.2) |
| E-15 | 41.3 (0.6) | 1284.8 | 23 (7.3) |
| E-16 | 34.4 (0.8) | 1205.8 | 98 (7.2) |

Example 7

Additive Manufacturing of 3D Printed Parts

The formulations of E-1, E-2, E-3, E-14 and E-15 resins were photopolymerized on the Asiga Pico 2 printer with a LED light source of 385 nm and ~23 mW/cm$^2$ of power. Tensile test bars of Type V according to ASTM D638-10 were manufactured. The following settings were used: Slice thickness=50 μm, Burn-In Layers=1, Separation Velocity=10 mm/s, Slides per Layer=1, Burn-In Exposure Time=20.0 s, Normal Exposure Time=3.5 s. The test bars were then cleaned in isopropanol to remove unreacted resin. The test bars were then post-cured under fusion lamps for 90 minutes on each side. The dogbones were kept in a vacuum oven at 80° C. overnight to remove any residual unreacted monomer. The post-cured dogbones were tested on an Insight MTS with 5 kN load cell at the rate of 5 mm/minute.

Five replicate samples were tested, and the average and standard deviation are reported. The tensile strength of the samples was determined according to ASTM D638-10 and shown in Table 5 below. Elongation at break was determined from the crosshead movement of the grips and the samples were not strain gauged.

TABLE 5

Tensile strength (MPa), Tensile Modulus (MPa) and Elongation at break (%) of 3D printed Formulations

| Sample ID | Tensile Strength (Std Dev) | Tensile Modulus (Std Dev) | Crosshead Elongation at Break (Std Dev) |
| --- | --- | --- | --- |
| E-1 | 43.2 (02) | 1552 | 93.4 (35.3) |
| E-2 | 32.5 (0.8) | 1090 | 114.7 (24.5) |
| E-3 | 39.2 (0.3) | 1091.6 | 80.1 (23.6) |
| E-14 | 39.2 (0.6) | — | 47.8 (9) |
| E-15 | 40.3 (0.4) | 1228.3 | 19 (11.5) |

Example 8

Quantifying Amount of Residual Monomers after Printing

E-3 squares (20 mm×20 mm×1 mm) were printed using the method described in Example 7. The printed samples (printed) were wiped with a KIMWIPE to remove excess residual monomer. The parts were post-cured under fusion lamps for 90 minutes on each side (postcured). The post-cured samples were then baked in the oven for 4 hours at 120° C. under vacuum to remove any residual unreacted monomers (baked). The percent unreacted monomers were quantified gravimetrically. Three squares at each stage were heated in the oven at 120° C. for 4 hours and the weight loss after that was reported as % residuals.

TABLE 6

Percent Residual Amount of Monomers for E-3 Printed Squares

| Stage | % Residuals Monomer (Std Dev) |
| --- | --- |
| Printed | 2.86 (0.19) |
| Postcured | 0.53 (0.02) |
| Baked | 0.00 (0) |

Example 9

Printing of Orthodontic Clear Tray Aligner

The formulation of E-2 was photopolymerized on the Asiga Pico 2 HD printer with a LED light source of 385 nm and ~16 mW/cm$^2$ of power. An STL file of the aligner was loaded into the software and support structures were generated. The resin bath of the printer was heated to 35-40° C. before photopolymerization to reduce the viscosity to be able to manufacture the article. The following settings were used: Slice thickness=50 μm, Burn-In Layers=1, Separation Velocity=10 mm/s, Slides per Layer=1, Burn-In Exposure Time=20.0 s, Normal Exposure Time=3.5 s. The photopolymerized aligners were then cleaned in isopropanol to remove unreacted resin and then post-cured under fusion lamps for 90 minutes on each side. The aligners were baked stepwise in a vacuum oven—30 minutes at 60° C., 1 hour at 80° C. followed by 4 hours at 100° C. to remove any unreacted monomers. The photopolymerized aligners fit the models, showing precision of the additive manufacture part. The aligners also had acceptable strength and flexibility.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. An article comprising a reaction product of a photopolymerizable composition, wherein the article is an orthodontic article, wherein the photopolymerizable composition comprises a blend of:
   a. 30 to 70 wt. %, inclusive, of at least one urethane component;
   b. 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius and wherein i) the at least one monofunctional reactive diluent comprises phenoxy ethyl methacrylate in an amount of 20 to 80 wt. % of the total amount of the at least one monofunctional reactive diluent, or ii) the at least one monofunctional reactive diluent is present in the form a prepolymer, or both i) and ii), and wherein the at least one monofunctional reactive diluent further comprises at least one monofunctional reactive diluent having a $T_g$ of 25 degrees Celsius or greater;
   c. optionally at least one multifunctional reactive diluent in an amount of 1 to 30 wt. %, inclusive, if present, based on the total weight of the photopolymerizable composition;
   d. 0.1 to 5 wt. %, inclusive, of at least one initiator; and
   e. an optional inhibitor in an amount of 0.001 to 1 wt. %, inclusive, if present, based on the total weight of the photopolymerizable composition.

2. The article of claim 1, wherein the at least one urethane component comprises a urethane (meth)acrylate, a urethane acrylamide, or combinations thereof, and wherein the at least one urethane component comprises a linking group selected from alkyl, polyalkylene, polyalkylene oxide, aryl, polycarbonate, polyester, polyamide, and combinations thereof.

3. The article of claim 1, wherein the at least one monofunctional reactive diluent comprises a compatibilizer present in an amount of at least 30 wt. % of the amount of the at least one urethane component.

4. The article of claim 1, wherein the at least one monofunctional reactive diluent comprises a (meth)acrylate, an alkyl (meth)acrylate, a phenoxy (meth)acrylate, a hydroxy alkyl (meth)acrylate, or a combination thereof.

5. The article of claim 1, wherein the at least one monofunctional reactive diluent comprises phenoxy ethyl methacrylate in an amount of 20 to 80 wt. % of the total amount of the at least one monofunctional reactive diluent.

6. The article of claim 1, wherein the at least one multifunctional reactive diluent is present and comprises a polyester methacrylate.

7. The article of claim 1, wherein the at least one monofunctional reactive diluent comprises a monofunctional reactive diluent exhibiting a hydrophilic-lipophilic balance (HLB) value of less than 10.

8. The article of claim 1, wherein the at least one initiator comprises a photoinitiator, a thermal initiator, or a combination thereof.

9. The article of claim 1, wherein the at least one monofunctional reactive diluent is present in the form a prepolymer.

10. The article of claim 1, wherein the at least one urethane component comprises at least one pendant group comprising a photoinitiator.

11. The article of claim 1, wherein the article comprises a plurality of layers.

12. The article of claim 1, exhibiting an elongation at break of 40% or greater.

13. The article of claim 1, exhibiting a tensile strength of 20 MegaPascals (MPa) or greater, as determined according to ASTM D638-10.

14. The article of claim 1, exhibiting a modulus of 500 MPa or greater, as determined according to ASTM D638-10.

15. A non-transitory machine readable medium comprising data representing a three-dimensional model of an orthodontic article, when accessed by one or more processors interfacing with a 3D printer, causes the 3D printer to create an article comprising a reaction product of a photopolymerizable composition comprising a blend of:
   a. 30 to 70 wt. %, inclusive, of at least one urethane component;
   b. 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius and wherein i) the at least one monofunctional reactive diluent comprises phenoxy ethyl methacrylate in an amount of 20 to 80 wt. % of the total amount of the at least one monofunctional reactive diluent, or ii) the at least one monofunctional reactive diluent is present in the form a prepolymer, or both i) and ii), and wherein the at least one monofunctional reactive diluent further comprises at least one monofunctional reactive diluent having a $T_g$ of 25 degrees Celsius or greater;
   c. optionally at least one multifunctional reactive diluent in an amount of 1 to 30 wt. %, inclusive, if present, based on the total weight of the photopolymerizable composition;
   d. 0.1 to 5 wt. %, inclusive, of at least one initiator; and
   e. an optional inhibitor in an amount of 0.001 to 1 wt. %, inclusive, if present, based on the total weight of the photopolymerizable composition.

16. A method comprising:
   a. receiving, by a manufacturing device having one or more processors, a digital object comprising data specifying a plurality of layers of an orthodontic article; and
   b. generating, with the manufacturing device by an additive manufacturing process, the article based on the digital object, the orthodontic article comprising a reaction product of a photopolymerizable composition, the photopolymerizable composition comprising a blend of:
      i. 30 to 70 wt. %, inclusive, of at least one urethane component;
      ii. 25 to 70 wt. %, inclusive, of at least one monofunctional reactive diluent, wherein the at least one monofunctional reactive diluent comprises at least one monofunctional reactive diluent having a $T_g$ of up to but not including 25 degrees Celsius and wherein i) the at least one monofunctional reactive diluent comprises phenoxy ethyl methacrylate in an amount of 20 to 80 wt. % of the total amount of the at least one monofunctional reactive diluent, or ii) the at least one monofunctional reactive diluent is present in the form a prepolymer, or both i) and ii), and wherein the at least one monofunctional reactive diluent further comprises at least one monofunctional reactive diluent having a $T_g$ of 25 degrees Celsius or greater;
      iii. optionally at least one multifunctional reactive diluent in an amount of 1 to 30 wt. %, inclusive, if present, based on the total weight of the photopolymerizable composition;
      iv. 0.1 to 5 wt. %, inclusive, of at least one initiator; and
      v. an optional inhibitor in an amount of 0.001 to 1 wt. %, inclusive, if present, based on the total weight of the photopolymerizable composition.

17. The article of claim 1, further comprising at least one filler selected the group consisting of from silica, alumina, zirconia, and discontinuous fibers.

* * * * *